(12) United States Patent
Eberwine et al.

(10) Patent No.: US 10,883,082 B2
(45) Date of Patent: Jan. 5, 2021

(54) TRANSCRIPTOME TRANSFER PRODUCES CELLULAR PHENOTYPE CONVERSION

(71) Applicant: The Trustees of the University of Pennsylvania, Philadelphia, PA (US)

(72) Inventors: James Eberwine, Philadelphia, PA (US); Jai-Yoon Sul, Bensalem, PA (US); Chia-Wen Wu, Philadelphia, PA (US); Fanyi Zeng, Philadelphia, PA (US); Junhyong Kim, Narbeth, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 14/230,848

(22) Filed: Mar. 31, 2014

(65) Prior Publication Data
US 2014/0206059 A1 Jul. 24, 2014

Related U.S. Application Data

(63) Continuation-in-part of application No. 12/086,471, filed on Jan. 31, 2012, and a continuation of application No. 12/755,277, filed as application No. PCT/US2006/047480 on Dec. 12, 2006.

(51) Int. Cl.
| | |
|---|---|
| C12N 5/0793 | (2010.01) |
| C12N 5/079 | (2010.01) |
| C12N 5/077 | (2010.01) |
| C12N 15/85 | (2006.01) |
| C12N 15/87 | (2006.01) |

(52) U.S. Cl.
CPC ........... *C12N 5/062* (2013.01); *C12N 5/0622* (2013.01); *C12N 5/0657* (2013.01); *C12N 15/85* (2013.01); *C12N 15/87* (2013.01); *C12N 2501/998* (2013.01); *C12N 2506/00* (2013.01); *C12N 2506/08* (2013.01); *C12N 2506/1307* (2013.01)

(58) Field of Classification Search
None
See application file for complete search history.

(56) References Cited

U.S. PATENT DOCUMENTS

| | | | |
|---|---|---|---|
| 3,711,262 | A | 1/1973 | Keck et al. |
| 5,034,506 | A | 7/1991 | Summerton et al. |
| 5,330,467 | A | 7/1994 | Abela |
| 5,891,634 | A | 4/1999 | Petri, Jr. et al. |
| 6,458,594 | B1 | 10/2002 | Baszczynski et al. |
| 6,753,161 | B2 | 6/2004 | Koller et al. |
| 6,973,245 | B2 | 12/2005 | Bocanegra et al. |
| 2004/0180430 | A1 | 9/2004 | West et al. |
| 2004/0235175 | A1 | 11/2004 | Gaudernack et al. |
| 2009/0068742 | A1 | 3/2009 | Yamanaka |
| 2011/0033934 | A1 | 2/2011 | Eberwine et al. |
| 2012/0129261 | A1 | 5/2012 | Eberwine et al. |
| 2012/0135493 | A1 | 5/2012 | Eberwine et al. |
| 2012/0178167 | A1 | 7/2012 | Eberwine et al. |

FOREIGN PATENT DOCUMENTS

| | | |
|---|---|---|
| EP | 0137504 | 1/1991 |
| EP | 1 083 232 A1 | 9/1999 |
| EP | 1 391 503 A1 | 12/2002 |
| EP | 1 270 732 | 1/2003 |
| EP | 1225228 | 8/2005 |
| JP | 2005-168495 | 6/2005 |
| WO | 1996/018741 | 6/1996 |
| WO | 99/14346 | 3/1999 |
| WO | 2001/075164 | 10/2001 |
| WO | 2002/090555 | 11/2002 |
| WO | 2003/079883 | 10/2003 |
| WO | 2005/044367 | 5/2005 |
| WO | 2006/059084 | 6/2006 |
| WO | 2007/047766 | 4/2007 |
| WO | 2007/084228 | 7/2007 |

OTHER PUBLICATIONS

U.S. Appl. No. 60/726,915, filed Oct. 14, 2005, Hu.
Guo Y. et al., "Laser-mediated gene transfer in rice", *Physiologia Plantatym*, 93 (19-24), 1995.
Palumbo G. et al., "Targeted gene transfer in eukaryotic cells by dye-assisted laser optoporation", *Journal of Photochemistry and Photobiology*, 36(1): 41-46, 1996.
Paterson L. et al., "Photoporation and cell transfection using a violet diode laser", *Optics Express*, 13(2): 595-600, 2005.
Smits E. et al., "RNA-based gene transfer for adult stem cells and T cells", *Leukemia*, 18: 1898-1902, 2004.
Tao W. et al., "Direct gene transfer into human cultured cells facilitated by laser micropuncture of the cell membrane", *Proceedings of the National Academy of Science USA*, 84: 4180-4184, 1987.
Tirlapur U. K. et al., "Targeted transfection by femtosecond laser", *Nature*, 418: 290-291, 2002.
Van Driessche A. et al., "Messenger RNA electroporation: an efficient tool in immunotherapy and stem cell research", *Folia Histochemica et Cytobiologica*, 43(4): 213-216,
Zeira E. et al., "Femtosecond Infrared Laser—An Efficient and Safe in Vivo Gene Delivery System for Prolonged Expression", *Molecular Therapy*, 8(2): 342-350, 2003.
Barrett Lindy E. et al., "Region-directed phototransfection reveals the functional significance of a dendritically synthesized transcription factor," Nature Methods, Jun. 2006, vol. 3, No. 6, pp. 455-460.
Bolstad et al., 2003, "A comparison of normalization methods for high density oligonucleotide array data based on variance and bias" Bioinformatics 19:185-193.

(Continued)

*Primary Examiner* — James D Schultz
(74) *Attorney, Agent, or Firm* — Riverside Law LLP

(57) ABSTRACT

The present invention includes methods for effecting phenotype conversion in a cell by transfecting the cell with phenotype-converting nucleic acid. Expression of the nucleic acids results in a phenotype conversion in the transfected cell. Preferably the phenotype-converting nucleic acid is a transcriptome, and more preferably an mRNA transcriptome.

18 Claims, 21 Drawing Sheets

Specification includes a Sequence Listing.

(56) References Cited

OTHER PUBLICATIONS

Chen, et al., 2005, "Ventilation-synchronous magnetic resonance microscopy of pulmonary structure and ventilation in mice" Magn. Reson. Med. 53: 69-75.
Dang, et al., 2005, "Comparison of histologic, biochemical, and mechanical properties of murine skin treated with the 1064-nm and 1320-nm Nd:YAG lasers" Exp Dermatol., 14: 876-882.
Eberwine et al., 1992, "Analysis of gene expression in single live neurons" PNAS 89: 3010-3014.
Eberwine, et al., 2001, "Analysis of mRNA populations from single live and fixed cells of the central nervous system". Current protocols in neuroscience (editorial board, Jacqueline N. Crawley et al.) Chapter 5, Unit 5.3.
Eberwine, 2001, "Single Cell Molecular Biology" Nat Neurosci. 4:1155-1156.
The Gene Ontology Consortium, 2000, "Gene ontology: tool for the unification of biology," Nature Genet. 25:25-29.
Hanna et al., 2007, "Treatment of sickle cell anemia mouse model with iPS cells generated from autologous skin" Science 318(5858):1920-1923.
Herberholz et al., 2002, "A Lateral Excitatory Network in the Escape Circuit of Crayfish" J Neurosci. 22: 9078-9085.
Huang et al., 2001, "A novel transcription factor inhibitor, SP100030, inhibits cytokine gene expression, but not airway eosinophilia or hyperresponsiveness in sensitized and allergen-exposed rat" Br. J. Pharmacol., 134: 1029-1036.
Huangfu D, et al. (2008) "Induction of pluripotent stem cells from primary human fibroblasts with only Oct4 and Sox2" Nat Biotechnol 26(11):1269-1275.
Kacharmina, et al., 2000, "Stimulation of glutamate receptor protein synthesis and membrane insertion within isolated neuronal dendrites" PNAS, 97:11545-11550.
Kim et al. (2008) "Pluripotent stem cells induced from adult neural stem cells by reprogramming with two factors" Nature 454(7204):646-650.
Maherali et al. (2007) "Directly reprogrammed fibroblasts show global epigenetic remodeling and widespread tissue contribution" Cell Stem Cell 1(1):55-70.
Martinez et al., 2002, "Single-Stranded Antisense siRNAs Guide Target RNA Cleavage in RNAi" Cell 110:563-74.
Mohanty, et al., 2003, "Laser-assisted microinjection into targeted animal cells" Biotechnol. Lett. 25: 895-899.
Nakagawa M, et al, 2008, "Generation of induced pluripotent stem cells without Myc from mouse and human fibroblasts" Nat Biotechnol 26(1):101-106.
Needham-VanDevanter, et al., 1984, "Characterization of an adduct between CC-1065 and a defined oligodeoxynucleotide duplex" Nucleic Acids Res., 12:6159-6168.
Neufeld et al., 1985, "Uptake and subcellular distribution of [3H]arachidonic acid in murine fibrosarcoma cells measured by electron microscope autoradiography" J Cell Biol. 101(2):573-581.
Okita et al., 2007, "Generation of germline-competent induced pluripotent stem cells" Nature 448(7151):313-317.
Roelandse, et al. 2004, "Hypothermia-Associated Loss of Dendritic Spines" J Neurosci. 24: 7843-7847.
Rowe et al. 2005, "Development of functional neurons from postnatal stem cells in vitro". Stem Cells 23(8):1044-1049.
Schneckenburger, et al., 2002, "Laser-assisted optoporation of single cells" J. Biomed. Opt., 7: 410-416.
Shirahata, et al., 2001, "New technique for gene transfection using laser irradiation" J. Invest. Med., 49: 184-190.
Soughayer, et al., 2000, "*Characterization of Cellular Optoporation with Distance*" Anal.Chem., 72: 1342-1347.
Stadtfeld et al., 2008, "Induced Pluripotent Stem Cells Generated Without Viral Integration" Science 322(5903):945-949.
Stracke et al., 2005, "Optical Nanoinjection of Macromolecules into Vital Cells" J Photochem Photobiol B 81:136-142, Abstract only.
Takahashi et al., 2006, "Induction of pluripotent stem cells from mouse embryonic and adult fibroblast cultures by defined factors" Cell 126(4):663-676.
Tang et al., 2006, "Efficient delivery of small interfering RNA to plant cells by a nanosecond pulsed laser-induced stress wave for posttranscriptional gene silencing," Plant Science 171:375-381.
Tirlapur et al., 2002, "Femtosecond near-infrared laser pulses as a versatile non-invasive tool for intra-tissue nanoprocessing in plants without comprising viability," The Plant Journal: for Cell and Molecular Biology, 31(3): 365-374.
Valles et al., 1997 "Ethanol exposure affects glial fibrillary acidic protein gene expression and transcription during rat brain development" J. Neurochem 69:2484-2493.
Van Gelder et al., 1990, "Amplified RNA synthesized from limited quantities of heterogeneous cDNA" PNAS 87 (5): 1663-1667.
Wernig et al., 2008, "Neurons derived from reprogrammed fibroblasts functionally integrate into the fetal brain and improve symptoms of rats with Parkinson's disease" PNAS 105(15):5856-5861.
Boczkowski et al., "Induction of Tumor Immunity and Cytotoxic T Lymphocyte Responses Using Dendritic Cells Transfected with Messenger RNA Amplified from Tumor Cells1", *Cancer Research*, 60: 1028-1034, Feb. 15, 2000.
Dannull et al., "Enhanced Antigen Presenting Function of Antigen-Loaded Dendritic Cells Following Cotransfection with OX40 Ligand mRNA", *Proceedings of the American Association for Cancer Research*, 45: 1-2, 2004.
Dannull et al., "Enhancing the Immunostimulatory Function of Dendritic Cells by Transfection with mRNA Encoding OX40 Ligand", *Blood*, 105(8): 3206-3213, Apr. 15, 2005.
Diaz et al., "Sindbis Viral Delivery of EGFP-Dopamine D1 Receptors into Native Neuronal Preparations", Program No. 160.14. 2003 Neuroscience Meeting Planner. New Orleans, LA; *Society for Neuroscience*, 2003, online (Abstract only).
Elango et al., "Optimized Transfection of mRNA Transcribed from a d (A/T) 100 Tail-Containing Vector", *Biochemical and Biophysical Research Communications*, 330: 958-966, 2005.
Fisher et al., "The Transmembrane Domain of Diphtheria Toxin Improves Molecular Conjugate Gene Transfer", *Biochemical Journal*, 321: 49-58, Jan. 1, 1997.
Kalady et al., "Sequential Delivery of Maturation Stimuli Increases Human Dendritic Cell IL-12 Production and Enhances Tumor Antigen-Specific Immunogenicity", *Journal of Surgical Research*, 116: 24-31, 2004.
Kim et al., "Transcriptome Transfer Provides a Model for Understanding the Phenotype of Cardiomyocytes", *PNAS Early Edition*, 2011, retrieved online: www.pnas.org/cgi/doi/10.1073/pnas.1101223108.
Malone et al., "Cationic Liposome-Mediated RNA Transfection", *Proceedings of the National Academy of Science*, 86: 6077-6081, Aug. 1989.
Nair et al., "Induction of Primary Carcinoembryonic Antigen (CEA)—Specific Cytotoxic T Lymphocytes in Vitro Using Human Dendritic Cells Transfected with RNA", *Nature Biotechnology*, 16: 364-369, Apr. 1998.
Rakhmilevich et al, "Eradication of Established Metastatic Murine Tumors Following Particle-Mediated Delivery of IL-12 Gene into the Skin", *Proceedings of the American Association for Cancer Research Annual*, 37: 347, Apr. 20-24, 1996.
Sawai Keisuke et al., "A Novel Method of Cell-Specific mRNA Transfection", *Molecular Genetics and Metabolism*, 64: 44-51, Jan. 7, 1998.
Petrova et al., 2002, "Lymphatic endothelial reprogramming of vascular endothelial cells by the Prox-1 homeobox transcription factor." The EMBO Journal, 21(17: 4593-4599.
Rakhmilevich et al., 2000, Gene Therapy of Cancer: Methods in Molecular Medicine, Ed, W. Walther and U. Stein, Humana Press, Inc. Totowa NJ, vol. 30: 331-344).
Boczkowski et al., 1996, "Dendritic Cells Pulsed with RNA are Potent Antigen-presenting Cells In Vitro and In Vivo." J. Exp. Med, 184: 465-472.
Izumikawa, et al., Mar. 2005, "Auditory hair cell replacement and hearing improvement by Atoh1 gene therapy in deaf mammals," *Nature Medicine*, vol. 11, No. 3, pp. 271-276.

(56) References Cited

OTHER PUBLICATIONS

Hu, Jifan: "U.S. Appl. No. 60/726,915, filed Oct. 14, 2005—Methods for Rejuvenating Cells In Vitro and in Vivo", European Patent Register Oct. 14, 2005 (Oct. 14, 2005), XP002787567, Retrieved from the Internet: URL:https://register.epo.org/application?documentId.ELXXBYJJ4843F14&number=EP0682619 28tlnpen&npl.false, 46 pages.

Kalady et al. "Dendritic Cells Pulsed With Pancreatic Cancer Total Tumor RNA Generate Specific Antipancreatic Cancer T Cells." J Gastrointest Surg 2004, 8:175-182 (Year: 2004).

Nencioni et al. "Dendritic cells transfected with tumor RNA for the induction of antitumor CTL in colorectal cancer." Cancer Gene Therapy (2003) 10, 209-214 (Year: 2003).

Sul, Jai-Yoon et al: "Transcriptome transfer produces a predictable cellular phenotype", Proceedings of the National Academy of Sciences of the United States of America, vol. 106, No. 18, May 5, 2009 (May 5, 2009), pp. 7624-7629, XP002787531, ISSN: 1091-6490.

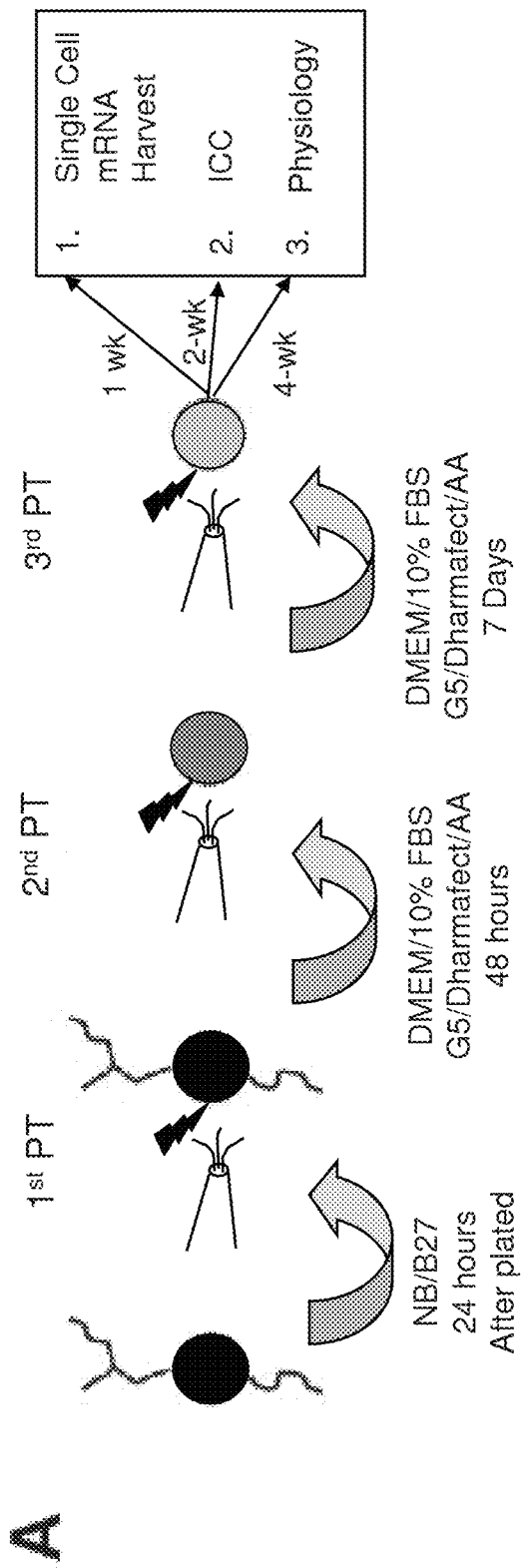

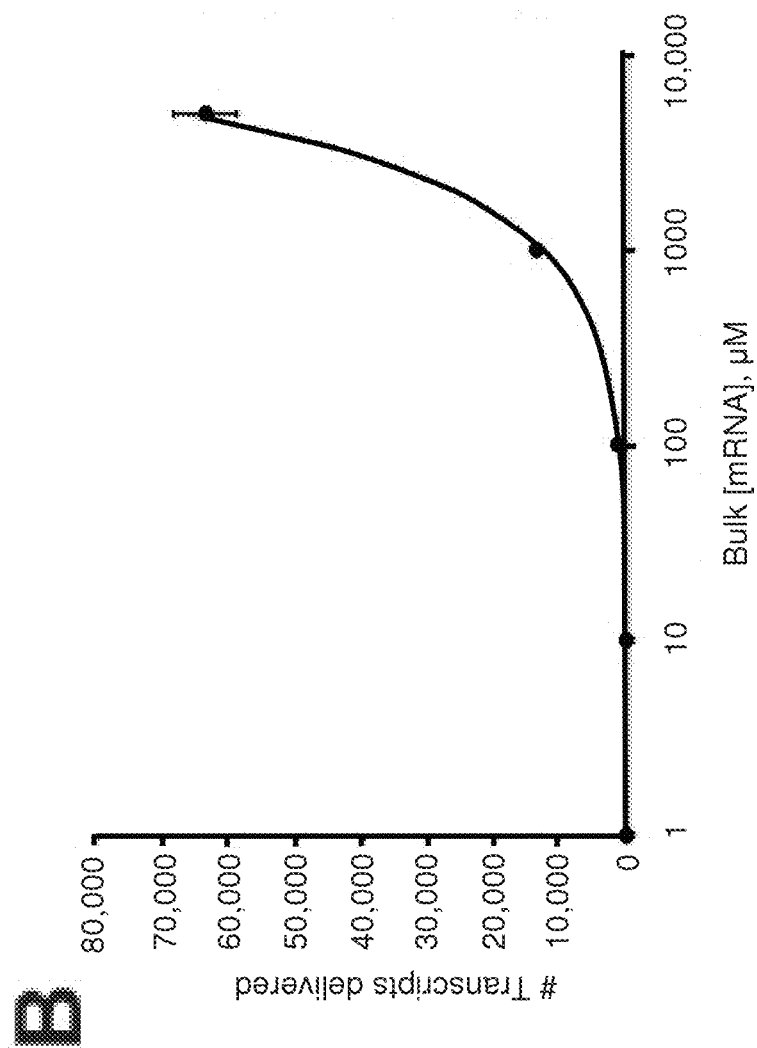

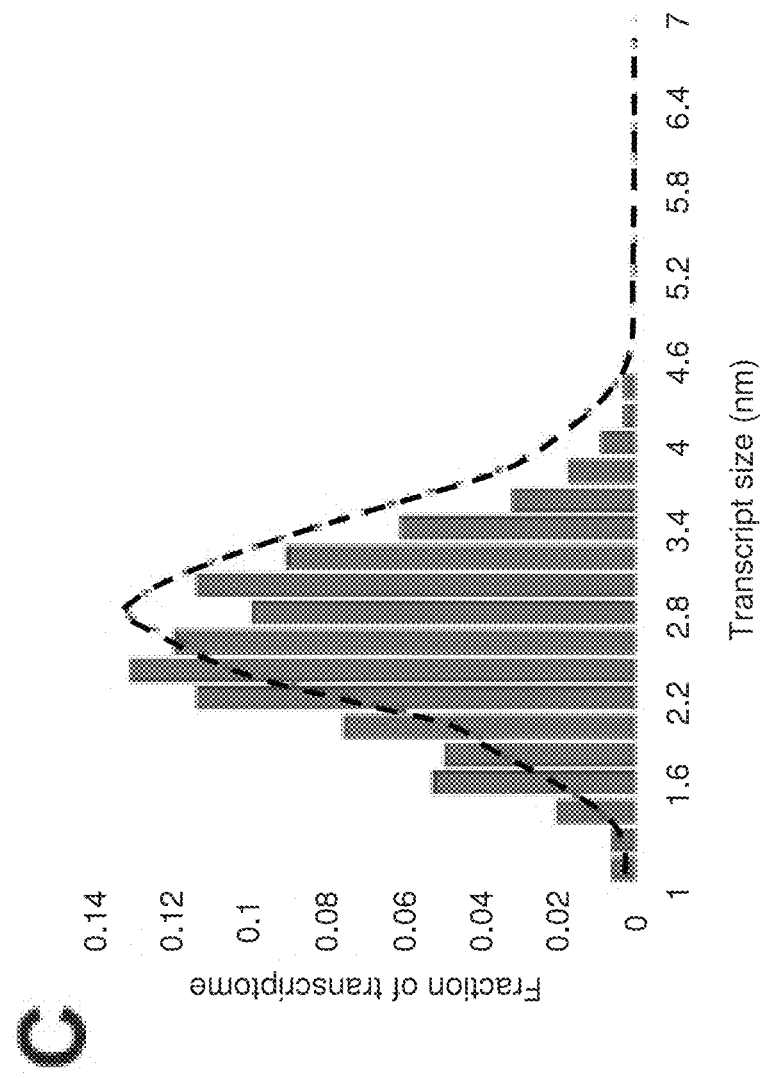

FIGURE 3A

|  |  | Primer Sets | |
| --- | --- | --- | --- |
| Cell Name | Age (week) | GFAP | MAP2 |
| 5-14-08 1/3 | 1 |  |  |
| 3-18-08 3/1 | 1 |  | + |
| 3-18-08 3/4 | 1 |  | + |
| 3-18-08 3/5 | 1 |  | + |
| 5-14-08 1/10 | 1 |  | + |
| 5-14-08 4/4 | 1 |  | + |
| 5-14-08 1/4 | 1 | + | + |
| 5-6-08 2/6 | 1 | + | + |
| 4-30-08 4/2 | 2 |  |  |
| 3-19-08 4/3 | 2 |  | + |
| 3-19-08 4/5 | 2 |  | + |
| 4-30-08 4/5 | 2 |  | + |
| 5-13-08 2/5 | 2 |  | + |
| 5-13-08 2/11 | 2 | + | + |
| 5-13-08 2/12 | 2 | + | + |
| 3-19-08 4/8 | 2 | + |  |
| 4-30-08 4/9 | 2 | + |  |
| 4-16-08 2/8 | 4 |  |  |
| 3-4-08 1/10 | 4 |  | + |
| 3-4-08 1/16 | 4 |  | + |
| 4-16-08 2/10 | 4 |  | + |
| 4-16-08 2/12 | 4 |  | + |
| 3-4-08 1/1 | 4 | + | + |
| 3-4-08 2/1 | 4 | + | + |
| 5-7-08 1/13 | 4 | + | + |
| 5-7-08 1/3 | 4 | + | + |
| Population cortex cells |  | + | + |
| No template |  |  |  | b c

FIGURES 4C-D
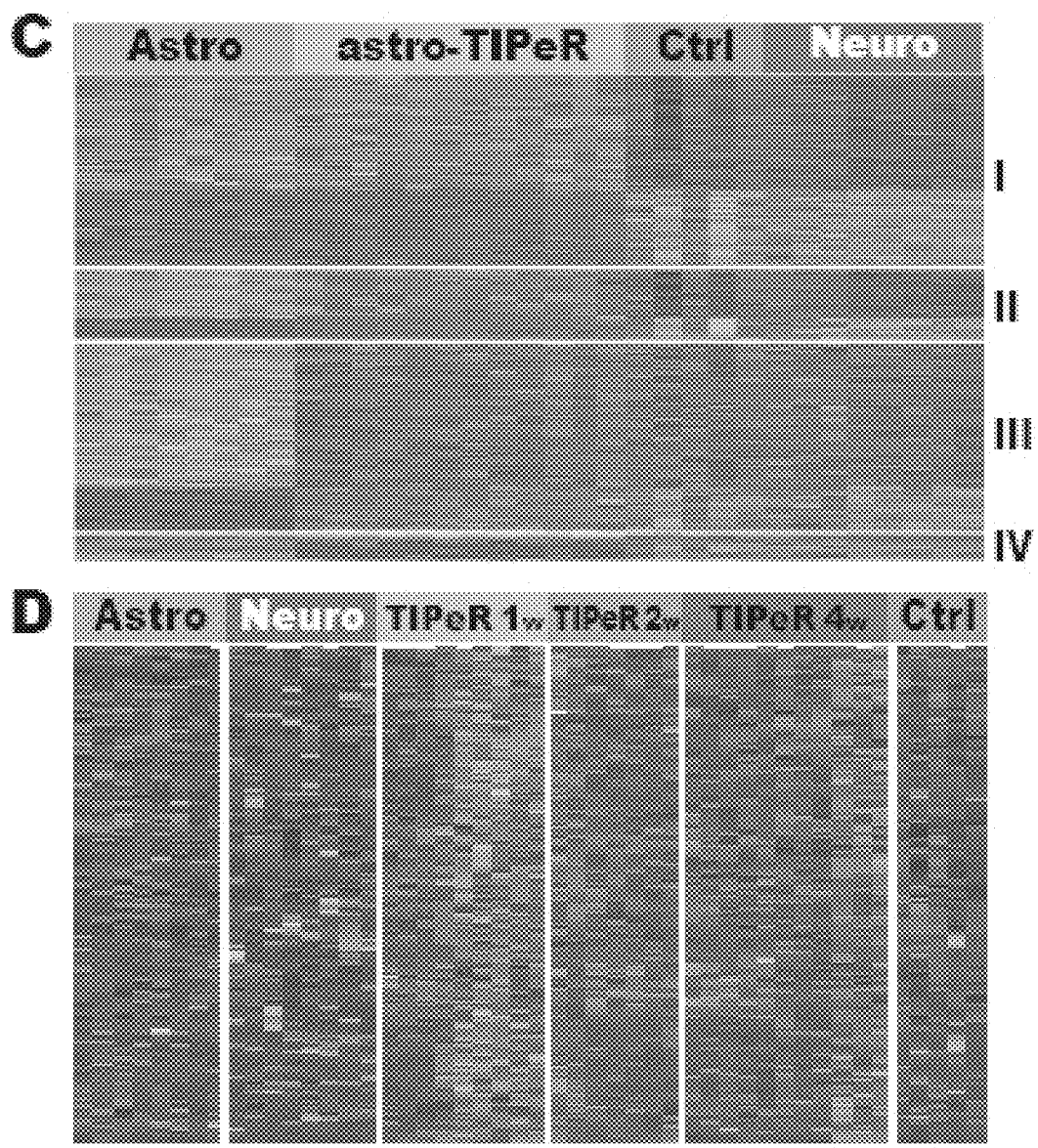

FIGURE 5A

| ProbeSet | Gene | Description | Wk- | Wk-1 | Wk- | Wk-2 | Wk- | Wk-4 | Ctrl | Ctrl |
|---|---|---|---|---|---|---|---|---|---|---|
| 1385407_at | AI511405 | TCDD-inducible poly(ADP-ribose) polymerase | + | 0.0002 | + | 0.0016 | + | 0.0237 | - | 0.9757 |
| 1382059_at | BI289529 | F-box protein 30 | + | 0.0005 | + | 0.1202 | + | 0.2552 | + | 0.284 |
| 1384742_at | BF389776 | a-thalassemia/mental retard. syndr. X-linked | + | 0.0005 | + | 0.0751 | + | 0.0264 | + | 0.3496 |
| 1397509_x_at | BI289049 | reproductive homeobox 9 | + | 0.0006 | + | 0.0768 | + | 0.0342 | + | 0.9483 |
| 1385098_at | AW526343 | Transcribed locus | + | 0.0006 | + | 0.3438 | + | 0.0571 | + | 0.6154 |
| 1380505_at | BF563556 | Transcribed locus | + | 0.0007 | + | 0.0228 | + | 0.1218 | - | 0.2182 |
| 1392405_at | AI177322 | transcription factor Dp-2 (E2F dimerization | + | 0.0008 | + | 0.5602 | + | 0.7142 | + | 0.5138 |
| 1387026_at | NM_031683 | structural maintenance of chromosomes 1A | + | 0.0012 | + | 0.3612 | + | 0.2202 | + | 0.9443 |
| 1382867_at | AA849390 | Transcribed locus | + | 0.0016 | + | 0.4462 | + | 0.0525 | - | 0.564 |
| 1382939_at | BE118639 | translocated promoter region | + | 0.0018 | + | 0.1843 | + | 0.0097 | + | 0.7047 |
| 1394412_at | AI144648 | transmembrane protein 16C (predicted) | + | 0.0022 | + | 0.0089 | + | 0.0566 | + | 0.9011 |
| 1378806_at | BF392451 | Transcribed locus | + | 0.0034 | + | 0.2395 | + | 0.1437 | - | 0.5261 |
| 1387687_at | NM_133542 | immunoglobulin superfamily, member 6 | + | 0.0044 | + | 0.1942 | + | 0.032 | - | 0.3368 |
| 1394530_at | AW535733 | Transcribed locus | + | 0.0047 | + | 0.0261 | + | 0.007 | - | 0.8455 |
| 1389644_at | BI289857 | WD repeat domain 67 | + | 0.0054 | + | 0.0721 | + | 0.1239 | - | 0.8642 |
| 1382263_at | AI511280 | outer dense fiber of sperm tails 2-like | + | 0.006 | + | 0.0017 | + | 0.1358 | + | 0.5245 |
| 1397657_at | BF416736 | --- | + | 0.0061 | + | 0.0549 | + | 0.0017 | + | 0.5215 |
| 1393804_at | BF388537 | similar to hypothetical protein FLJ22490 | + | 0.0071 | + | 0.0095 | + | 0.0331 | - | 0.6432 |
| 1370710_at | L78306 | acetylserotonin O-methyltransferase | + | 0.0078 | + | 0.2795 | + | 0.0572 | - | 0.8589 |
| 1393041_at | AW535052 | structural maintenance of chromosomes 2 | + | 0.0086 | + | 0.2259 | + | 0.4666 | + | 0.6075 |
| 1375405_at | BF405058 | Transcribed locus | + | 0.0088 | + | 0.0062 | + | 0.0648 | + | 0.5731 |
| 1393733_at | BF402788 | phosphatidic acid phosphatase type 2 | + | 0.0101 | + | 0.0244 | + | 0.1756 | - | 0.5793 |
| 1394844_s_at | AA893326 | cytochrome P450, family 4, subfamily a | + | 0.0102 | + | 0.2175 | + | 0.5733 | + | 0.8503 |
| 1384250_a_at | AA818098 | Transcribed locus | + | 0.0106 | + | 0.0367 | + | 0.141 | + | 0.9681 |

FIGURE 5B

| ProbeSet | Gene | Description | Wk- | Wk-1 | Wk- | Wk-2 | Wk- | Wk-4 | Ctrl | Ctrl |
|---|---|---|---|---|---|---|---|---|---|---|
| 1375263_at | BI296498 | Transcribed locus | + | 0.0109 | + | 0.4928 | + | 0.048 | + | 0.4626 |
| 1371290_a_at | U68491 | 5-hydroxytryptamine (serotonin) receptor 7 | + | 0.0114 | + | 0.2559 | + | 0.0077 | + | 0.7705 |
| 1393834_at | BF402667 | Transcribed locus | + | 0.0116 | + | 0.3644 | + | 0.4757 | + | 0.9256 |
| 1388627_at | AI179261 | cathepsin Q | + | 0.012 | + | 0.0339 | + | 0.0127 | - | 0.605 |
| 1380831_at | AI237035 | Transcribed locus | + | 0.0123 | + | 0.2868 | + | 0.0693 | + | 0.5335 |
| 1370738_a_at | AF220558 | triadin | + | 0.0125 | + | 0.1007 | + | 0.1279 | - | 0.886 |
| 1398063_x_at | BI282513 | cystatin A (stefin A) (predicted) /// stefin A3 | + | 0.0128 | + | 0.0844 | + | 0.041 | - | 0.3283 |
| 1396635_at | BF409915 | --- | + | 0.0131 | + | 0.0537 | + | 0.1366 | + | 0.697 |
| 1379945_at | AI137329 | kelch repeat and BTB (POZ) domain containing | + | 0.0176 | + | 0.3897 | - | 0.2536 | - | 0.7847 |
| 1384520_at | AW523106 | Transcribed locus | + | 0.0194 | + | 0.3551 | + | 0.1677 | - | 0.5042 |
| 1380804_at | BM391896 | Transcribed locus | + | 0.0197 | + | 0.2126 | + | 0.679 | - | 0.1963 |
| 1393051_at | BF551457 | armadillo repeat containing, X-linked 1 | + | 0.0204 | + | 0.9599 | - | 0.5853 | + | 0.4487 |
| 1385248_a_at | AA997590 | osteoglycin | + | 0.0209 | + | 0.0838 | + | 0.1456 | - | 0.9416 |
| 1384147_at | AA955540 | eukaryotic translation initiation factor 1A | + | 0.0211 | - | 0.4863 | - | 0.8579 | + | 0.6111 |
| 1382982_at | AI230669 | Transcribed locus | + | 0.0219 | + | 0.5439 | + | 0.2396 | - | 0.8116 |
| 1380443_at | AA893371 | PWP1 homolog (S. cerevisiae) (predicted) | + | 0.0223 | + | 0.1795 | + | 0.0757 | + | 0.5897 |
| 1388176_at | AI717047 | camello-like 5 | + | 0.0225 | + | 0.4831 | + | 0.2965 | - | 0.4634 |
| 1379934_at | BI285676 | Transcribed locus | + | 0.0228 | + | 0.4767 | + | 0.1396 | + | 0.9129 |
| 1396846_at | AW527501 | --- | + | 0.0249 | - | 0.95 | + | 0.1327 | + | 0.7305 |
| 1385327_at | AW522979 | protocadherin beta 13 | + | 0.0295 | - | 0.9473 | + | 0.2548 | - | 0.8495 |
| 1372954_at | BF404393 | Sprague-Dawley UV73 mRNA, partial | + | 0.0336 | + | 0.2868 | + | 0.285 | + | 0.425 |
| 1393878_at | BF416495 | Transcribed locus | + | 0.0364 | + | 0.265 | + | 0.3236 | - | 0.9 |
| 1369421_at | NM_022615 | topoisomerase (DNA) I | + | 0.0396 | - | 0.3115 | + | 0.8003 | - | 0.7872 |
| 1393701_at | BF397095 | debranching enzyme homolog 1 (S. cerevisiae) | + | 0.0484 | - | 0.9579 | + | 0.2006 | + | 0.5603 |

FIGURE 5C

| | | | | | | | | |
|---|---|---|---|---|---|---|---|---|
| 1395224_at | AI102342 | Rho GTPase activating protein 21 (predicted) | + | 0.0493 | + | 0.0978 | + | 0.5895 |
| 1389666_at | AA892855 | rod outer segment membrane protein 1 | + | 0.0528 | + | 0.0778 | + | 0.9959 |
| 1393586_at | AI101752 | neighbor of Punc E11 (predicted) | + | 0.0567 | + | 0.1771 | - | 0.762 |
| 1375195_at | BG376894 | Transcribed locus | + | 0.0594 | + | 0.0192 | + | 0.6612 |
| 1388528_at | AW433875 | fibrillarin | + | 0.0598 | + | 0.0465 | - | 0.891 |
| 1387118_at | NM_013105 | cytochrome P450, family 3, subfamily a | + | 0.078 | + | 0.0451 | - | 0.8619 |
| 1379837_at | AI548995 | Transcribed locus | + | 0.0794 | + | 0.034 | + | 0.3407 |
| 1379227_at | BF392832 | Transcribed locus | + | 0.0823 | + | 0.0197 | - | 0.7459 |
| 1370498_at | AF296762 | ABO blood group | + | 0.0927 | + | 0.115 | + | 0.8364 |
| 1383187_a_at | AA944136 | Transcribed locus | + | 0.102 | + | 0.006 | - | 0.6219 |
| 1394654_at | BF398431 | zinc finger protein 451 | + | 0.1081 | + | 0.0678 | + | 0.729 |
| 1369910_at | NM_139193 | prolactin releasing hormone receptor | + | 0.1331 | + | 0.0506 | - | 0.8672 |
| 1390769_at | AI535312 | ribose-phosphate pyrophosphokinase I -like | + | 0.1598 | + | 0.1425 | - | 0.3963 |
| 1393362_at | AI554982 | Transcribed locus | + | 0.3038 | + | 0.0036 | - | 0.5552 |
| 1378531_at | AI555775 | Transcribed locus | - | 0.3523 | - | 0.8244 | - | 0.5819 |
| 1380935_at | AI179379 | Transcribed locus | + | 0.4975 | + | 0.2182 | + | 0.6637 |
| 1395423_at | AW920217 | Transcribed locus | + | 0.5555 | + | 0.6157 | - | 0.9838 |

FIGURE 6

| Aspect | Term | p-value |
|---|---|---|
| MF | chromatin binding | 1.30E-02 |
| CC | chromosome | 1.60E-02 |
| MF | protein binding | 3.00E-02 |
| BP | sister chromatid segregation | 3.20E-02 |
| BP | mitotic sister chromatid segregation | 3.20E-02 |
| MF | binding | 3.80E-02 |
| BP | DNA repair | 3.80E-02 |
| BP | cellular component organization and biogenesis | 4.60E-02 |
| BP | response to DNA damage stimulus | 5.80E-02 |
| BP | chromosome segregation | 6.60E-02 |
| MF | nucleoside-triphosphatase activity | 8.00E-02 |
| CC | chromosomal part | 8.10E-02 |
| BP | DNA metabolic process | 8.10E-02 |
| MF | pyrophosphatase activity | 8.80E-02 |
| MF | hydrolase activity, acting on acid anhydrides, in phosphorus-containing anhydrides | 8.90E-02 |
| MF | hydrolase activity, acting on acid anhydrides | 9.10E-02 |

FIGURE 7A

| Aspect | Term | p-value |
|---|---|---|
| *Ia: Expression higher in Astro-TiPeRs and astrocytes compared to neurons* | | |
| MF | RNA polymerase II transcription factor activity | 2.64E-05 |
| MF | nucleic acid binding | 4.08E-04 |
| BP | transcription from RNA polymerase II promoter | 1.37E-03 |
| BP | RNA metabolic process | 2.64E-03 |
| BP | gene expression | 5.57E-03 |
| BP | positive regulation of transcription, DNA-dependent | 6.54E-03 |
| MF | general RNA polymerase II transcription factor activity | 6.64E-03 |
| MF | DNA binding | 8.59E-03 |
| BP | transcription, DNA-dependent | 1.22E-02 |
| BP | transcription | 1.22E-02 |
| BP | RNA biosynthetic process | 1.24E-02 |
| BP | nucleobase, nucleoside, nucleotide and nucleic acid metab. | 1.39E-02 |
| BP | positive regulation of transcription | 1.45E-02 |
| BP | regulation of myeloid cell differentiation | 1.66E-02 |
| BP | transcription initiation | 1.74E-02 |
| BP | pos. regul. of nucleo-base, -side, -tide & nucleic acid metab. | 1.76E-02 |
| BP | regulation of transcription from RNA polymerase II promoter | 1.79E-02 |
| MF | transcription regulator activity | 1.81E-02 |
| BP | reg. of nucleo-base, -side, -tide & nucleic acid metabolic process | 2.16E-02 |
| MF | structure-specific DNA binding | 2.26E-02 |
| BP | regulation of cellular metabolic process | 2.39E-02 |
| CC | DNA-directed RNA polymerase II, holoenzyme | 2.40E-02 |
| BP | response to stress | 2.92E-02 |
| BP | regulation of metabolic process | 3.49E-02 |
| BP | regulation of transcription | 3.58E-02 |
| BP | positive regulation of cellular metabolic process | 3.59E-02 |
| MF | RNA polymerase II transcription mediator activity | 4.03E-02 |
| BP | regulation of transcription, DNA-dependent | 4.05E-02 |
| MF | nucleotide binding | 4.22E-02 |
| BP | biopolymer metabolic process | 4.39E-02 |
| BP | positive regulation of metabolic process | 4.63E-02 |
| CC | nucleoplasm part | 4.69E-02 |
| BP | cellular metabolic process | 4.84E-02 |

FIGURE 7B

| | Ib: Expression lower in Astro-TIPeRs and astrocytes compared to neurons | |
|---|---|---|
| BP | cell division | 4.45E-04 |
| BP | cytokinesis | 4.80E-03 |
| MF | nucleotide binding | 5.89E-03 |
| BP | biological regulation | 5.93E-03 |
| MF | binding | 7.67E-03 |
| BP | regulation of biological process | 7.92E-03 |
| MF | amino acid transmembrane transporter activity | 1.38E-02 |
| BP | amino acid transport | 2.42E-02 |
| MF | carboxylic acid transmembrane transporter activity | 2.90E-02 |
| MF | organic acid transmembrane transporter activity | 2.96E-02 |
| BP | regulation of cellular process | 3.03E-02 |
| MF | L-glutamate transmembrane transporter activity | 3.24E-02 |
| MF | acidic amino acid transmembrane transporter activity | 3.24E-02 |
| MF | purine ribonucleotide binding | 3.55E-02 |
| MF | ribonucleotide binding | 3.55E-02 |
| BP | amine transport | 3.60E-02 |
| BP | dicarboxylic acid transport | 3.61E-02 |
| BP | cellular component organization and biogenesis | 4.18E-02 |
| MF | protein binding | 4.36E-02 |
| BP | carboxylic acid transport | 4.51E-02 |
| MF | purine nucleotide binding | 4.53E-02 |
| BP | organic acid transport | 4.58E-02 |
| | II: Expression in Astro-TIPeRs intermediate between astrocytes and neurons | |
| MF | catalytic activity | 3.10E-03 |
| CC | outer membrane | 1.34E-02 |
| MF | pyrophosphatase activity | 1.58E-02 |
| MF | hydrolase act., acting on acid anhydrides, in P-containing anhydrides | 1.62E-02 |
| MF | hydrolase act., acting on acid anhydrides | 1.68E-02 |
| CC | envelope | 2.64E-02 |
| CC | organelle envelope | 2.64E-02 |

FIGURE 7C

| | IIIa: Expression higher in Astro-TIPeRs and neurons compared to astrocytes | |
|---|---|---|
| BP | glutamine metabolic process | 3.41E-03 |
| CC | spindle | 5.12E-03 |
| CC | spindle pole | 5.74E-03 |
| CC | chromosome | 7.98E-03 |
| BP | mitosis | 9.94E-03 |
| BP | M phase of mitotic cell cycle | 1.09E-02 |
| MF | binding | 1.20E-02 |
| BP | mitotic cell cycle | 1.30E-02 |
| CC | nuclear chromosome | 1.33E-02 |
| CC | organelle part | 1.62E-02 |
| CC | chromosomal part | 1.85E-02 |
| CC | vesicle membrane | 1.96E-02 |
| BP | cell cycle phase | 1.97E-02 |
| CC | membrane-bound organelle | 2.00E-02 |
| BP | glutamine family amino acid metabolic process | 2.19E-02 |
| CC | intracellular | 2.58E-02 |
| BP | metabolic process | 2.91E-02 |
| BP | M phase | 2.96E-02 |
| CC | intracellular organelle part | 3.00E-02 |
| CC | microtubule cytoskeleton | 3.01E-02 |
| CC | intracellular membrane-bound organelle | 3.39E-02 |
| MF | nucleic acid binding | 3.66E-02 |
| CC | organelle | 3.87E-02 |
| BP | nitrogen compound metabolic process | 4.40E-02 |
| BP | cell cycle process | 4.65E-02 |
| CC | intracellular non-membrane-bound organelle | 4.82E-02 |
| CC | non-membrane-bound organelle | 4.82E-02 |
| BP | regulation of mitosis | 4.99E-02 |

FIGURE 7D

| | IIIb: Expression lower in Astro-TiPeRs and neurons compared to astrocytes | |
|---|---|---|
| MF | oxidoreductase activity, acting on superoxide radicals as acceptor | 1.21E-02 |
| MF | superoxide dismutase activity | 1.21E-02 |
| BP | response to drug | 1.79E-02 |
| MF | binding | 3.14E-02 |
| BP | superoxide metabolic process | 3.24E-02 |
| CC | envelope | 3.36E-02 |
| CC | organelle envelope | 3.36E-02 |
| CC | mitochondrion | 4.61E-02 |
| | IVa: Expression higher in Astro-TiPeRs compared to astrocytes and neuron | |
| MF | nucleic acid binding | 4.20E-02 |
| BP | transport | 4.55E-02 |
| | IVb: Expression lower in Astro-TiPeRs compared to astrocytes and neurons | |
| CC | intracellular | 2.14E-03 |
| CC | intracellular membrane-bound organelle | 3.63E-03 |
| CC | membrane-bound organelle | 3.66E-03 |
| CC | intracellular part | 9.05E-03 |
| CC | intracellular organelle | 1.34E-02 |
| CC | organelle | 1.36E-02 |
| BP | protein transport | 1.37E-02 |
| BP | aldehyde metabolic process | 1.59E-02 |
| BP | establishment of protein localization | 1.70E-02 |
| BP | protein localization | 2.03E-02 |
| MF | binding | 2.11E-02 |
| BP | macromolecule localization | 2.28E-02 |

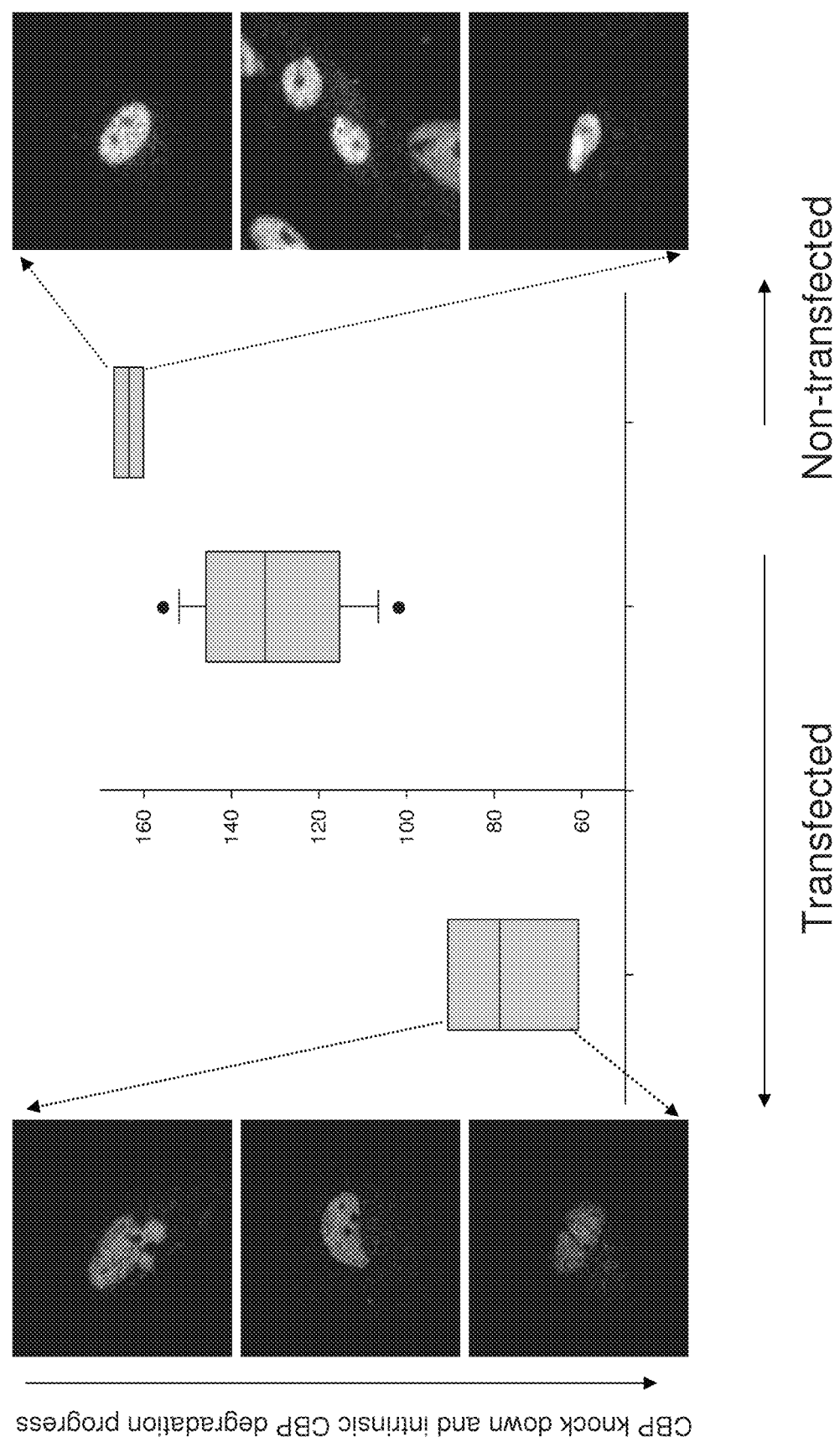

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial
<220> FEATURE:
<223> OTHER INFORMATION: Chemically synthesized

<400> SEQUENCE: 1
agtggccacc agtaacatgc aa                                              22
```

<210> SEQ ID NO 2
<211> LENGTH: 22
<212> TYPE: DNA
<213> ORGANISM: Artificial
<220> FEATURE:
<223> OTHER INFORMATION: Chemically synthesized

<400> SEQUENCE: 2
ttgtcttgct ccagcagcct at                                          22

<210> SEQ ID NO 3
<211> LENGTH: 22
<212> TYPE: DNA
<213> ORGANISM: Artificial
<220> FEATURE:
<223> OTHER INFORMATION: Chemically synthesized

<400> SEQUENCE: 3
agaaaccagc ctggacacca aa                                          22

<210> SEQ ID NO 4
<211> LENGTH: 22
<212> TYPE: DNA
<213> ORGANISM: Artificial
<220> FEATURE:
<223> OTHER INFORMATION: Chemically synthesized

<400> SEQUENCE: 4
tgggaattgg gcctagcaaa ca                                          22

<210> SEQ ID NO 5
<211> LENGTH: 22
<212> TYPE: DNA
<213> ORGANISM: Artificial
<220> FEATURE:
<223> OTHER INFORMATION: Chemically synthesized

<400> SEQUENCE: 5
atggccacca agaccttgga aa                                          22

<210> SEQ ID NO 6
<211> LENGTH: 22
<212> TYPE: DNA
<213> ORGANISM: Artificial
<220> FEATURE:
<223> OTHER INFORMATION: Chemically synthesized

<400> SEQUENCE: 6
acggactttg tcatcggttc ct                                          22

<210> SEQ ID NO 7
<211> LENGTH: 22
<212> TYPE: DNA
<213> ORGANISM: Artificial
<220> FEATURE:
<223> OTHER INFORMATION: Chemically synthesized

<400> SEQUENCE: 7
tggagggcaa actacccaag tt                                          22

<210> SEQ ID NO 8
<211> LENGTH: 22
<212> TYPE: DNA
<213> ORGANISM: Artificial
<220> FEATURE:
<223> OTHER INFORMATION: Chemically synthesized -continued

```
<400> SEQUENCE: 8
atcagcaaca ggtggcaaac ca                                              22
```

TRANSCRIPTOME TRANSFER PRODUCES CELLULAR PHENOTYPE CONVERSION

CROSS-REFERENCE TO RELATED APPLICATIONS

This application is a continuation of U.S. application Ser. No. 12/755,277, filed on Apr. 6, 2010, which is a continuation-in-part of U.S. application Ser. No. 12/086,471, filed on Jan. 31, 2012, which is the National Stage application of PCT International Application No. PCT/US2006/047480, filed on Dec. 12, 2006, and claims priority to U.S. Provisional Application No. 60/749,941, filed on Dec. 13, 2005, and U.S. Provisional Application No. 61/167,286, filed on Apr. 7, 2009, each of which applications is hereby incorporated by reference in its entirety herein.

STATEMENT REGARDING FEDERALLY SPONSORED RESEARCH OR DEVELOPMENT

This invention was made with government support under grant numbers OD004117 and MH014654 awarded by the National Institutes of Health. The government has certain rights in the invention.

BACKGROUND OF THE INVENTION

Cellular phenotype is the conglomerate of multiple cellular processes involving gene and protein expression that result in the elaboration of a cell's particular morphology and function. It has been thought that differentiated post-mitotic cells have their genomes hard wired with little ability for phenotypic plasticity. Emerging evidence has, however, demonstrated the reversibility and flexibility of the cellular phenotype. It has been shown that fertile adult male and female frogs can be obtained by injecting endoderm nuclei into enucleated eggs (Gurdon J B, Elsdale T R, & Fischberg M (1958) Sexually mature individuals of *Xenopus laevis* from the transplantation of single somatic nuclei. *Nature* 182(4627):64-65). This result not only forms the foundation of the field in nuclear transplantation, but also provides evidence that the cytoplasmic components of a differentiated cell can support nuclear reprogramming. Generation of induced pluripotent stem (iPS) cells by transfection transcription factors into dividing fibroblasts (Takahashi K & Yamanaka S (2006) Induction of pluripotent stem cells from mouse embryonic and adult fibroblast cultures by defined factors. *Cell* 126(4):663-676), followed by cell selection represent a new strategy to globally revert a mature cell into a different cell type. See: Huangfu D, et al. (2008) Induction of pluripotent stem cells from primary human fibroblasts with only Oct4 and Sox2. *Nat Biotechnol* 26(11):1269-1275; Kim J B, et al. (2008) Pluripotent stem cells induced from adult neural stem cells by reprogramming with two factors. *Nature* 454(7204):646-650; Nakagawa M, et al. (2008) Generation of induced pluripotent stem cells without Myc from mouse and human fibroblasts. *Nat Biotechnol* 26(1): 101-106; Maherali N, et al. (2007) Directly reprogrammed fibroblasts show global epigenetic remodeling and widespread tissue contribution. *Cell Stem Cell* 1(1):55-70; Okita K, Ichisaka T, & Yamanaka S (2007) Generation of germline-competent induced pluripotent stem cells. *Nature* 448 (7151):313-317; and Stadtfeld M, Nagaya M, Utikal J, Weir G, & Hochedlinger K (2008) Induced Pluripotent Stem Cells Generated Without Viral Integration. *Science* 322(5903): 945-949. The need for re-differentiation of these ES-like-iPS cells into desired cell types, however, adds a layer of complexity that is difficult to control (Wernig M, et al. (2008) Neurons derived from reprogrammed fibroblasts functionally integrate into the fetal brain and improve symptoms of rats with Parkinson's disease. *Proc Natl Acad Sci USA* 105(15):5856-5861; Hanna J, et al. (2007) Treatment of sickle cell anemia mouse model with iPS cells generated from autologous skin. *Science* 318(5858):1920-1923). Nevertheless, studies of nuclear reprogramming from genomic and epigenetic modification, as seen from somatic-cell-nuclear-transfer-cloned animals and iPS cells, suggests the flexibility of a differentiated phenotype as well as the dynamic changes of a genome (Maherali N, et al. (2007) Directly reprogrammed fibroblasts show global epigenetic remodeling and widespread tissue contribution. *Cell Stem Cell* 1(1):55-70).

Despite the development and refinement of the techniques discussed above, there remains a need in the art for methods and compositions for effecting phenotypic change in a cell. This invention addresses that need.

BRIEF SUMMARY OF THE INVENTION

The present invention encompasses a method of effecting phenotype conversion in a cell. The method comprises transfecting a second cell, the recipient cell, having a particular phenotype with phenotype-converting nucleic acid from a first cell, the donor cell, having a particular phenotype, wherein the phenotype of the first cell is different from that of the second cell. In some embodiments, the phenotype of the first cell differs from the phenotype of the second cell by one or more of: species, tissue type, differentiation degree, disease state, exposure to a toxin, exposure to a pathogen, and exposure to a candidate therapeutic. Optionally, the method further comprises transfecting the second cell at least a second time with the first cell mRNA transcriptome.

Preferably, the phenotype-converting nucleic acid is the transcriptome and more preferably the mRNA transcriptome of the first cell. In one embodiment, the mRNA transcriptome comprises mRNA transcripts having an average size between about 1 kb to about 5 kb.

In some embodiments, the phenotype-converting nucleic acid further comprises one or more exogenous nucleic acids selected from the group consisting of mRNA, siRNA, miRNA, hnRNA, tRNA, non-coding RNA and combinations thereof.

In some embodiments, the transfecting step comprises irradiating the cell with a laser, wherein the cell is bathed in a fluid comprising the first cell mRNA transcriptome. Optionally, the irradiating step can comprise 2 to 25 laser excitation pulses, wherein the laser is directed to different site on the second cell for each laser excitation pulse.

In some embodiments, the second cell is contacted with an exogenous transcription inhibition agent prior to the transfecting step. Alternatively, in other embodiments, the second cell is not substantially contacted with an exogenous transcription inhibition agent before, during or after the transfecting step.

In some embodiments, the cell is selected from the group consisting of a eukaryotic cell and a prokaryotic cell. The eukaryotic cell can be a non-mammalian cell or it can be a mammalian cell. In some embodiments, the eukaryotic cell is a human cell.

In some embodiments, phenotype conversion comprises a change in one or more of gene expression, protein expression, immunological markers, morphology, physiology, synthesis of bioproducts, and membrane lipid composition. In some embodiments, phenotype conversion comprises a change in expression of at least 100 genes. Phenotype conversion can comprise up-regulation of genes associated with chromosomal remodeling. In some embodiments, at least about 5% of differentially expressed genes in the second cell change expression to a level observed for the first cell.

In some embodiments, phenotype conversion persists for at least 2 weeks. In other embodiments, phenotype conversion persists for the lifetime of the cell.

In one embodiment, the second cell is a hair cell that responds to a first range of sound frequencies. Optionally, the first cell is a hair cell that responds to a second range of sound frequencies.

In another aspect, the invention provides a method of preparing a cell enriched for the presence of a second messenger system pathway. The method comprises the steps of transfecting a heterogenous collection of mRNAs encoding the components of a second messenger system pathway into a cell, wherein expression of the transfected heterogenous collection of mRNAs enriches the presence of the second messenger system pathway. Optionally, the method further comprising transfecting the cell with siRNA corresponding to one or more components of a different second messenger system pathway, thereby reducing expression of the components of the different second messenger system pathway.

In yet another aspect, the invention provides a method of deleting a gene of interest in a cell. The method comprises transfecting an mRNA encoding an enzyme capable of sequence specific excision into a cell. The cell comprises chromosomal material that comprises a gene of interest flanked by recognition sequences specific for the enzyme capable of sequence specific excision. Expression of the mRNA provides the enzyme capable of sequence specific excision. The enzyme then binds to the enzyme recognition sequences and excises the gene of interest. The enzyme capable of sequence specific excision can be selected from the group consisting of CRE recombinase, FLP recombinase, zinc finger nuclease and combinations thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A-1C depict a representative timeline for an embodiment of the method of the invention, and graphs relating to characterization of a representative transcriptome. FIG. 1A depicts a representative timeline of sequential phototransfections. A first phototransfection (PT) was performed on hippocampal neurons, with local delivery of the astrocyte transcriptome. The same procedure was repeated 48 hrs and 7 days after the first phototransfection. Single cell mRNA harvesting, immunocytochemistry and physiological assessment were performed at various times subsequent to the third phototransfection. FIG. 1B is a graph of simulation data developed to estimate the efficacy of mRNA transfer though a standard phototransfection pulse. Transport of molecules across the plasma membrane using phototransfection with laser irradiation can be controlled through both the number of pulses and extracellular nucleic acid concentrations in the method. FIG. 1C is a histogram (dashed line) of the size distribution of the transcripts in solution during an exemplary phototransfection. The bars show the amount of the transcript delivered into the cytosol for a given transcript size.

FIG. 2A depicts a schematic of laser excitation pulses and resultant membrane permeability. FIG. 2B is a schematic depicting 16 separate regions (shaded ovals) of laser excitation (250 nm in diameter). A distribution of membrane pore sizes (bottom schematic) is assumed to form in each region of laser excitation. Although the exact pore size is not known, it is assumed that the distribution of pore sizes were Gaussian, as depicted in the graph on the bottom right.

FIGS. 3A to 3C are a series of a table, images and a graph related to expression of astrocytic and neuronal mRNA and protein markers in neuronal cells transfected with astrocyte transcriptomes (N-TIPeR-AS cells). FIG. 3A is a table summarizing single cell RT-PCR results. Single cell RT-PCR was performed on N-TIPeR-AS cells at different time points to detect the expression of GFAP and MAP2 genes. Age was defined as time post the third phototransfection. "+" indicates the presence of GFAP or MAP2 mRNA. GFAP positive cells are highlighted in light gray. A population of brain cortex cells containing both neurons and astrocytes were used as positive control. Water was the negative control. FIG. 3B is a series of images of a representative N-TIPeR-AS cell immunostained for all NeuN, GFAP and fibronectin antibodies two weeks post the third phototransfection. Scale bar=10 µm. FIG. 3C is a graph depicting results of immunocytochemistry studies of neurons, astrocytes and N-TIPeR-AS cells. The graph shows that integrated immunofluorescence signal from regions of interest. Immunoreactivity was tested for Dynamin 1 and GFAP. Astrocyte (triangle). Neuron (square). TIPeR cell (circle).

FIGS. 4A-4D are graphs and images depicting global gene expression patterns of TIPeR cells. FIG. 4A is a schematic depicting UPGMA clustering of the cell conditions on 3104 informative genes, with major branches labeled with bootstrap support indicating confidence in each cluster. Leaves are colored different shades of gray according to cell type: charcoal=neurons (N); dark gray =N-TIPeR-N controls (C); light gray=astrocyte (Astro)s; white=TIPeRed cells (TIPeR). FIG. 4B is a graph of the 3104-dimensional standard gene space reduced to three dimensions of biological interest: 1st axis representing genes most variable for astrocyte vs neurons, $2^{nd}$ axis representing genes most variable between the TIPeR cells (i.e., representing TIPeR treatment variability), and the $3^{rd}$ axis representing overall variability of all cells (astrocytes; neurons; control; neuro-TIPeR; astro-TIPeR, i.e., the TIPeR cells clustering closest to the astrocytes as shown in the dendrogram in 4A). The transparent "cloud" around the points shows non-parametric density contours. FIG. 4C is an image of a heatmap showing intensity of 512 distinguishing probes across astrocytes (Astro), astro-TIPeRs (astro-TIPeR), N-TIPeR-N controls (Ctrl), and neurons (Neuro). Probes are separated by white lines into four groups according to the intensities of the astro-TIPeR cells compared to the intensities of the neurons and the astrocytes: (I) astro-TIPeR expression is similar to astrocytes but not neurons (201 probes); (II) astro-TIPeR expression is intermediate between astrocytes and neurons (77 probes); (III) astro-TIPeR expression is similar to neurons but not astrocytes (202 probes); (IV) astro-TIPeR expression is dissimilar to both neurons and astrocytes (32 probes). Each lane is the data from an individual cell. FIG. 4D is an image of a heatmap of 171 probes that are significantly quiescent in both astrocytes (Astro) and neurons (Neuro); followed in TIPeR cells 1 week (TIPeR 1w), 2 weeks (TIPeR 2w), and 4 weeks (TIPeR 4w) post phototransfection; and for control cells (Ctrl). Each lane is the data from an individual cell.

FIGS. 5A-5C depict a table of genes activated after TIPeR. The table lists the 65 probes (out of 171 probes) with significantly low expression levels in astrocytes and neurons that are significantly up-regulated in N-TIPeR-AS cells. Gene annotations and p-value for each group are listed. Significant (p<0.05) p-values are bolded.

FIG. 6 is a table of GO terms enriched in the N-TIPeR-AS. The table lists the significant GO annotation terms enriched among 49 genes up-expressed in the N-TIPeR-AS cells 1-wk post the last transfection. Aspect abbreviations: MF=molecular function, CC=cellular component, BP=biological process.

FIGS. 7A-7D depict a table of data related to GO enrichment analysis. Analysis was on sets of probes distinguishing different cell conditions: GO aspect (Biological Process, Cellular Component, Molecular Function), term, and enrichment p-value for significantly enriched GO annotation terms among each subset of genes showing differential expression among the different cell conditions, as labeled.

FIG. 8A is a series of DIC images of a representative N-TIPeR-N cell (left panel) and an representative N-TIPeR-AS cell (right panel). Scale bar=20 μm. FIG. 8B is a bar graph or relative cell size of N-TIPeR-N cells cultured in the neuronal medium (NB), N-TIPeR-N cells and N-TIPeR-AS cells. The Y-axis is the percentage of change in overall cell size when comparing that of post-TIPeR to the initial cell size. Error bars represent the value of standard error of the mean (SEM). FIG. 8C is a bar graph regarding process retraction for N-TIPeR-N cells cultured in the neuronal medium (NB), N-TIPeR-N cells and N-TIPeR-AS cells. Process retraction occurs for N-TIPeR-As cells with 65% of N-TIPeR-AS cells showing retraction of their processes while only 40% of N-TIPeR-N cells cultured in the astrocyte medium and 20% of N-TIPeR-N cells cultured in the neuronal medium retracted their processes. The dark gray bars correspond to % cells retaining neuronal processes. The black bars correspond to % cells that have lost neuronal processes.

FIG. 11 is a graph and a series of images depicting representative levels of CBP immunoreactivity in mouse cells transfected with mRNA encoding CRE-recombinase and non-transfected mouse cells. The mouse cells were obtained from a mouse genetically engineered to have the gene for CBP300 flanked by Lox P sites. The X axis is transfected or non-transfected cells. Cells were transfected with two different quantities of mRNA; the data on the far left is for cells transfected with 10-fold more mRNA than the data depicted in the middle of the graph. The Y axis is the fluorescence intensity of CBP staining, which is a reflection of the amount of CBP protein present in a cell. The data depicted was obtained 7 days after transfection.

Figures 2A, 2B:
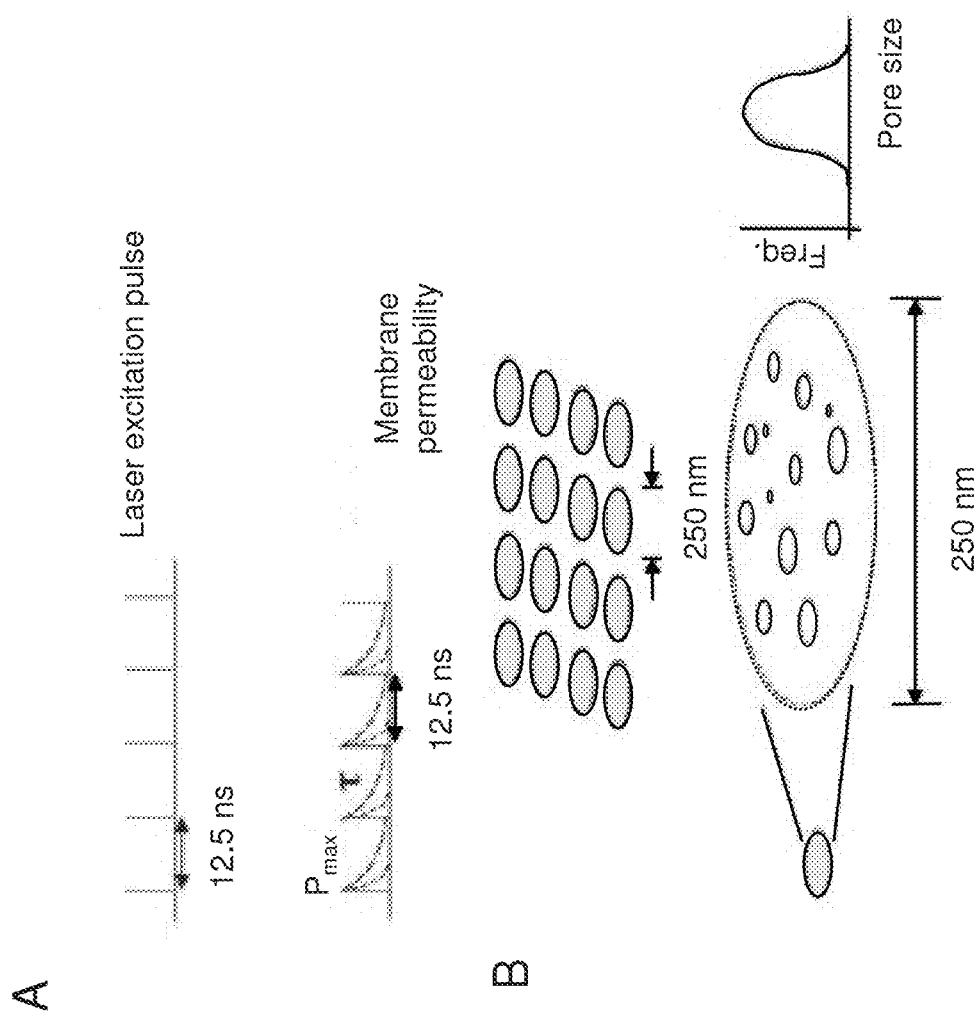
FIGS. 2A and 2B depict schematics related to simulations of the phototransfection procedure.

DETAILED DESCRIPTION OF THE INVENTION cDNA microarray analysis has shown that phenotypic differences at the cellular level are associated with differences in the presence, absence and abundances of particular RNAs. The invention described herein arises from the discovery that the relative abundances of RNAs within a population themselves can elaborate cellular phenotype. Specifically, the invention provides a method of effecting a phenotype conversion in recipient cell by introducing phenotype-converting nucleic acid from a donor cell into the recipient cell. In a preferred embodiment, the phenotype-converting nucleic acid is the mRNA transcriptome of the donor cell. The discovery described herein indicates that the plasticity of the non-dividing genome is much greater than previously imagined.

Phenotype-converting nucleic acid may include, without limitation, mRNA, siRNA, microRNA, tRNA, hnRNA, total RNA, DNA, and combinations thereof, such that the introduction of these nucleic acids into a cell and the subsequent expression of these nucleic acids results in a combined phenotype due to the multiple expression of these nucleic acids and their interactions with each other. Unlike expression systems known in the art, where one or only a few nucleic acids are expressed, the methods of the present invention permit the expression of multiple nucleic acids essentially simultaneously, resulting in an expression system closely mirroring the interaction of various nucleic acids and their expression products in a natural environment. Thus, the present invention permits the introduction of a complex mixture of nucleic acids into a cell to produce a multigenic effect, thereby effecting phenotype conversion of a cell.

The methods of the present invention are performed by transfecting a mixture of nucleic acids into live cells. In a preferred embodiment, the present invention includes methods for phenotype conversion of a cell using laser-aided poration of live cell membranes coupled with bath application of nucleic acids, preferably a transcriptome, in order to transfect a mixture of nucleic acids into a live cell. Photoporation is advantageous in enabling highly location-specific transfection of a cell and permitting multiple poration events, while not detrimental to cellular function or viability.

The present invention permits the transfection of nucleic acid, preferably mRNA and/or DNA into a cell with accurate control of the amount of nucleic acid entering the cell, thus allowing the skilled artisan to mimic the expression level of nucleic acid in a cell under desired conditions, as disclosed elsewhere herein. That is, the present invention allows the skilled artisan to accurately control the level of nucleic acid transfected into a cell by modulating the concentration of nucleic acid in the extracellular environment of the cell. Further, the precise amount of nucleic acid transfected into a cell can be modulated through regulation of laser intensity, pore size and number, and duration of membrane opening, as well as repetition of transfection.

The methods of the present invention are not limited to cells, but can further include live slices of tissue and live animals, preferably mammals, as disclosed elsewhere herein. The methods of the present invention can further comprise other non-mammalian cells eukaryotic cells and prokaryotic cells, such as bacterial cells, yeast cells, plant cells, protozoa, insect cells, fungal cells, including filamentous and non-filamentous fungi, and the like.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, "phenotype conversion" refers to the induction or establishment of a destination phenotype. Phenotype conversion comprises a change in at least one of gene expression, protein expression, immunological markers, morphology, physiology, synthesis of bioproducts (e.g., dopamine) and membrane lipid composition.

As used herein, a "destination phenotype" refers to a phenotype of interest that is induced in a recipient cell by the introduction therein of a mixture of nucleic acids. The phenotype of interest may be any phenotype. For example, a destination phenotype may be a morphological change, such as the retraction of neuronal processes in a recipient cell that is a neuron. A destination phenotype may be a physiological change, such as the presence of voltage-gated calcium receptors in a recipient cell that is an astroglial cell. A destination phenotype may comprise more than one phenotypic change and may even cause the cell to assume characteristics of a different tissue type from its original tissue type.

The phrase "phenotype-converting nucleic acid" refers herein to a mixture of nucleic acid that is capable of establishing a destination phenotype in a recipient cell. Phenotype-converting nucleic acid is not limited to the empirical content of RNA in a donor cell, but rather, encompasses the relative abundance of each RNA with respect to each in a population of RNAs such that the population of RNAs are necessary and sufficient to induce a destination phenotype in a recipient cell.

As used herein, "transcriptome" refers to the collection of all gene transcripts in a given cell and comprises both coding RNA (mRNAs) and non-coding RNAs (e.g., siRNA, miRNA, hnRNA, tRNA, etc). As used herein, an "mRNA transcriptome" refers to the population of all mRNA molecules present (in the appropriate relative abundances) in a given cell. An mRNA transcriptome comprises the transcripts that encode the proteins necessary to generate and maintain the phenotype of the cell. As used herein, an mRNA transcriptome may or may not further comprise mRNA molecules that encode proteins for general cell existence, e.g., housekeeping genes and the like.

As used herein, "TIPeR" refers to the process of transfecting a recipient cell with a transcriptome from a donor cell. A cell that has undergone this process may be referred to herein as a TIPeRed cell.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A "fluid medium" or "fluid media" is used herein to refer to a form of matter, such as air, liquid, solid or plasma, preferably liquid, that is capable of flowing.

An "isolated cell" refers to a cell which has been separated from other components and/or cells which naturally accompany the isolated cell in a tissue or mammal.

As applied to a protein, a "fragment" of a polypeptide, protein or an antigen, is about 6 amino acids in length. More preferably, the fragment of a protein is about 8 amino acids, even more preferably, at least about 10, yet more preferably, at least about 15, even more preferably, at least about 20, yet more preferably, at least about 30, even more preferably, about 40, and more preferably, at least about 50, more preferably, at least about 60, yet more preferably, at least about 70, even more preferably, at least about 80, and more preferably, at least about 100 amino acids in length amino acids in length, and any and all integers there between.

A "genomic DNA" is a DNA strand which has a nucleotide sequence homologous with a gene as it exists in the natural host. By way of example, a fragment of a chromosome is a genomic DNA.

As used herein, an "inhibitory nucleic acid" refers to an siRNA, a microRNA, an antisense nucleic acid or a ribozyme.

As used herein, "locally transfecting" a nucleic acid refers to introducing a nucleic acid into a region of cytoplasm that is not the entirety of the cytoplasm of a cell optionally comprising a cellular process.

As used herein, "porate" or "porates" refers to creating a hole in a surface through which compounds can pass.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are completely or 100% homologous at that position. The percent homology between two sequences is a direct function of the number of matching or homologous positions, e.g., if half (e.g., five positions in a polymer ten subunits in length) of the positions in two compound sequences are homologous then the two sequences are 50% identical, if 90% of the positions, e.g., 9 of 10, are matched or homologous, the two sequences share 90% homology. By way of example, the DNA sequences 5'ATTGCC3' and 5'TATGGC3' share 50% homology.

In addition, when the terms "homology" or "identity" are used herein to refer to the nucleic acids and proteins, it should be construed to be applied to homology or identity at both the nucleic acid and the amino acid sequence levels.

The term "multigenic phenotype" is used herein to refer to a phenotype in a cell, tissue or animal that is mediated by the expression or lack of expression of two or more nucleic acids encoding a protein, wherein the nucleic acids are exogenously provided to the cell, tissue or animal.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Phototransfection" is used herein to refer to a process by which a hole is created in a barrier, such as a cell membrane, using a photon source, such as a laser, and two or more nucleic acids, wherein the nucleic acids encode different polypeptides, are inserted into a cell through the hole in the cell membrane.

By "tag" polypeptide is meant any protein which, when linked by a peptide bond to a protein of interest, may be used to localize the protein, to purify it from a cell extract, to immobilize it for use in binding assays, or to otherwise study its biological properties and/or function.

It is understood that any and all whole or partial integers between any ranges set forth herein are included herein.

Description

The present invention provides methods of introducing mixtures of nucleic acids into a recipient cell to produce a phenotype-conversion in the recipient cell. The present invention comprises transfecting phenotype-converting nucleic acid, preferably RNA and/or DNA, even more preferably mRNA, and most preferably, an mRNA transcriptome, locally into a recipient cell. The phenotype of the donor cell is different from the phenotype of the recipient cell. The difference in phenotype may be any difference, such a difference in species, tissue type, extent of differentiation, exposure to a drug or pathogen, disease state, growth conditions and so forth, wherein the difference is known or suspected of resulting from a difference in gene expression.

As shown herein, transfection with an mRNA transcriptome yields a high degree of phenotype conversion. Where multiple cells are transfected in accordance with the method of the invention, at least about 25% of the cells undergo phenotype conversion. In some embodiments, phenotype conversion in at least about 35% of recipient cells is observed.

The recipient cell may be any type of cell. A recipient cell may be an eukaryotic cell or a prokaryotic cell. When the cell is an eukaryotic cell, the cell is preferably a mammalian cell, including but not limited to human, non-human primate, mouse, rabbit, rat, goat, guinea pig, horse cell, and the like. A non-mammalian eukaryotic cell includes a yeast cell, a plant cell, an insect cell, a protozoan cell and a fungal cell, including filamentous and non-filamentous fungi. When the cell is a prokaryotic cell, the cell is a bacterial cell. A recipient cell may be a differentiated cell and/or a non-dividing cell. The cell may also be a progenitor cell or a stem cell. Preferably, the recipient cell is a tissue-specific cell, more preferably a mammalian tissue-specific cell and more preferably still, a human tissue-specific cell. Non-limiting examples of cells suitable as recipient cells include epithelial cells, neurons, fibroblasts, embryonic fibroblasts, keratinocytes, adult stem cells, embryonic stem cells, and cardiomyocytes.

To obtain the desired phenotype conversion, recipient cells are preferably phenotypically-pliable cells. Phenotypically-pliable cells are cells whose phenotype is amenable to changing under the conditions of the method of the invention. Non-limiting examples of phenotypically-pliable cells include neurons, fibroblasts, embryonic fibroblasts, adult stem cells and embryonic stem cells. Preferably, the cell is a neuron, and comprises a cellular process such as a dendrite, and the nucleic acid is RNA, even more preferably, mRNA and more preferably still, an mRNA transcriptome.

In the method of the invention, nucleic acid is transferred into a cell to initiate phenotype conversion in the recipient cell. As used herein, phenotype conversion comprises a change in at least one of gene expression, protein expression, immunological markers, morphology, physiology, synthesis of bioproducts (e.g., dopamine) and membrane lipid composition. Preferably, the change yields a phenotype associated with or indicative of the cell from which the transfected RNA or DNA is obtained. Preferably, phenotype conversion in the recipient cell comprises two or more changes. More preferably, phenotype conversion comprises three or more changes. In one embodiment, phenotype conversion comprises a change in physiology. In another embodiment, phenotype conversion comprises a change in morphology and a change in physiology of the recipient cell. As shown herein, phenotype conversion may be accompanied by changes in expression in hundreds of genes. For instance, expression of genes quiescent in both the donor and the recipient cells may be de novo up-regulated. Genes associated with chromosomal remodeling, such as genes involved in chromosome and DNA metabolism related process, may be up-regulated in cells having phenotype conversion. See "BP" terms in FIGS. 6 and 7. Genes annotated "BP" in the Gene Ontology ("GO") database are considered associated with chromosomal remodeling (The Gene Ontology Consortium (2000) "Gene ontology: tool for the unification of biology," Nature Genet. 25:25-29). The GO database is publicly available (see www(dot)geneontology(dot)org). In some embodiments, at least about 5%, more preferably about 7%, 10%, 15% and more preferably still at least about 25% of genes that are expressed differently in the recipient cell compared to the donor cell (e.g., differentially expressed genes) based on gene expression profiling have their expression changed to the level observed for the donor cell.

Phenotype conversion in the recipient cell is maintained stably for extended periods of time. In one embodiment, phenotype conversion is stable and persists for at least about 1 day, 2 days, 3 days, 4 days, 5 days, 6 days, 7 days, 8 days, 9 days, 10 days, 11 days, 12 days, 13 days, or more. In one embodiment, phenotype conversion is stable for at least about 1 week, 2 weeks, 3 weeks, 4 weeks, or more. In another embodiment, phenotype conversion is stable for at least about 1 month, 2 month, 3 months or more. In preferred embodiments, phenotype conversion is stable for the duration of the recipient cell's lifespan or the lifespan of a culture derived from the recipient cell.

Phenotype-converting nucleic acid may comprise two or more nucleic acids having different sequences. In some embodiments, the two or more nucleic acids encode different polypeptides. In other embodiments, the nucleic acids are non-coding RNAs or other non-coding nucleic acids. In yet other embodiments, the nucleic acids comprise a mixture of coding and non-coding nucleic acids. In preferred embodiments, the phenotype-converting nucleic acid comprises the transcriptome, preferably the mRNA transcriptome, from a donor cell. In other embodiments, the phenotype-converting nucleic consists only of the transcriptome or mRNA transcriptome from a donor cell. Nucleic acids may be obtained from a donor cell or may be chemically synthesized or a combination thereof. Methods for chemically synthesizing a nucleic acid are disclosed elsewhere herein and can include in vitro transcription.

An mRNA transcriptome may comprise mRNAs encoding 3 or more, 5 or more, 10 or more, 20 or more, 40 or more, 50 or more, 75 or more, 100 or more, 200 or more different polypeptides.

The method of the invention may be carried on a cell comprising a cellular process. Such a cellular process includes, but is not limited to, a dendrite, an axon, a microvilli, a cilia, a stereocilia, a process, an astrocytic process, and the like. As demonstrated herein, this method advantageously permits the introduction of a desired amount of nucleic acid into one or more local sites, permitting the controlled and localized production of protein in physiological amounts, resulting in a multigenic effect in a cell. This method thus allows specific localization of exogenously applied nucleic acid, preferably mRNA, without resorting to severing the cellular process from the cell to which it is attached (Kacharmina, et al., 2000, Proc. Nat'l Acad. Sci. USA, 97:11545-11550). Further, the present method permits the expression of an mRNA transcriptome of a donor cell, thus resulting in phenotype conversion in the recipient cell.

The present invention further comprises methods for phototransfecting a live slice of tissue or a live animal. Methods for sustaining the cellular processes in the cells comprising a live slice of tissue are known in the art. As a non-limiting example, live slices can be refrigerated and perfused with natural or artificial fluids, such as artificial spinal fluid, artificial central nervous system fluid, and buffers disclosed elsewhere herein. Methods for the manipulation of live slice cultures are described in, for example, Roelandse, et al. (2004, J. Neuroscience, 24: 7843-7847); and Chen, et al. (2005, Magn. Reson. Med. 53: 69-75).

Methods for phototransfecting a live animal, preferably a mammal, are performed using the methods described herein combined with methods of animal and human surgery known in the art. Exemplary surgical procedures contemplated for use with the methods of the invention include cardiac catherization, angioplasty, arthroscopy, laproscopy, tumor resection, surgical placement of a therapeutic implant and the like. Mammals contemplated in the present invention include, but are not limited to, mice, rabbits, rats, goats, guinea pigs, humans, and the like.

As a non-limiting example, a laser is applied to a tissue in a live animal to phototransfect the tissue in the live animal with one or more nucleic acids. The nucleic acid is introduced to the animal using methods disclosed elsewhere herein, such as through a microscope or an optical fiber or endoscopy. The expression of a polypeptide phototransfected using the methods of the present invention is monitored using methods of detecting protein expression known in the art, such as Western blots, immunocytochemistry, in situ protein detection, and the like. Methods for using a laser to manipulate animal tissues are well known in the art and are described in, for example, Dang, et al. (2005, Exp Dermatol., 14: 876-882).

The methods disclosed herein comprise introducing phenotype-converting nucleic acid, preferably RNA and more preferably mRNA, siRNA, miRNA, hnRNA, tRNA, non-coding RNAs and combinations thereof, including but not limited to total mRNA, to a cell that optionally comprises a cellular process, preferably a neuron comprising a dendrite, and phototransfecting the cell at one or more sites on the cell membrane. Preferably, the phenotype-converting nucleic acid introduced into a cell optionally comprising a cellular process is an mRNA transcriptome. The cell is preferably a primary cell culture or in slice culture. The cell optionally comprising a cellular process can be phototransfected at any site. Preferably, the site is on a cellular process, such as a dendrite, or the cell body, such as the soma. The nucleic acid can be provided to the cell comprising a cellular process by any method known to the skilled artisan, and is preferably provided by means of a nucleic acid bath comprising a mixture of nucleic acids, disclosed elsewhere herein. A nucleic acid bath is a solution comprising a nucleic acid of interest in which a cell is bathed. In one embodiment, bath application of the cell comprises surrounding the cell with a solution comprising nucleic acid, thus bathing the entire cell. The cell is then irradiated with a laser at one or more sites located anywhere on the cell. In another embodiment, bath application comprises bathing a discrete portion or portions of a live cell, for instance, by applying a solution comprising nucleic acid to a discrete location on the surface of the cell. The cell is then irradiated one or more times within the discrete location or locations that was bathed. The discrete location bath is advantageous because it creates a greater mRNA concentration gradient, which allows mRNAs to diffuse more efficiently through the temporary poration holes into the porated cell. It also requires less mRNAs (e.g., 0.3 μg) than the bath application (e.g., 20 μg). In either case, the solution is appropriately buffered and is of the proper pH to maintain the structural integrity of the cell to be phototransfected.

Phenotype-converting nucleic acid suitable for use in the method of the invention may be of any size. For instance, a nucleic acid of about 800 nucleotides and a nucleic acid of about 3000 nucleotides have been successfully phototransfected into cells comprising a cellular process using the inventive procedure. However, the methods of the present invention are not limited to a nucleic acid, preferably an RNA, of the sizes disclosed herein. The present invention comprises phototransfecting a nucleic acid of about 30 bases, even more preferably, about 50 bases, yet more preferably, about 75 bases, even more preferably, about 100 bases, yet more preferably, about 75 bases, even more preferably, about 100 bases, yet more preferably, about 150 bases, even more preferably, about 200 bases, yet more preferably, about 300 bases, even more preferably, about 500 bases, yet more preferably, about 750 bases, even more preferably, about 1000 bases, yet more preferably, about 1500 bases, even more preferably, about 2000 bases, yet more preferably, about 2500 bases, even more preferably, about 3000 bases, in length. Even more preferably, the present invention comprises transfecting, preferably by phototransfection, a mixture of RNAs encoding different proteins and of different molecular weights. In preferred embodiments, the phenotype-type converting nucleic acid is an mRNA transcriptome having a range of mRNA transcript sizes and having an average mRNA transcript size from about 0.5 kb to about 5 kb, more preferably, from about 1 kb to about 3.5 kb. As a non-limiting example, the mRNA transcriptome is obtained from an astrocyte, wherein the average size of the mRNA transcriptome is about 1.5 kb. The transcriptome is transfected into a recipient cell, such as a neuron, to induce phenotype conversion of the neuron to the astrocyte phenotype.

As another non-limiting example, a nucleic acid expression profile of a cell in a desired physiological state (e.g. during differentiation, in a disease state, after treatment with a pharmaceutical, toxin or other compound) and a nucleic acid expression profile of a cell in another physiological state (e.g. the same cell type pre- or post-differentiation, not in a disease state, or before treatment with a pharmaceutical, toxin or other compound) can be obtained using techniques for RNA isolation known in the art and disclosed elsewhere herein. The cDNA clones of these RNAs can be generated, reflecting the altered RNA abundances of the differing physiological states, or the RNA can be transfected into a cell without first reverse transcribing the RNA to cDNA. These RNA can be mixed according to the same ratios and abundances indicated by the nucleic acid expression profiles of the cells in differing physiological states. These nucleic acid mixtures are then transfected into a cell using the phototransfection methods disclosed herein. The methods of the present invention permit the local transfection of a cell, and therefore the nucleic acid mixture can be locally transfected to a specific part of a cell, such as the soma, an astrocytic process, a dendrite, or another cellular process, or the nucleic acid mixture can be generally transfected into a cell by phototransfecting any portion of the cell. Using the methods of the present invention, and the physiologically relevant mixtures of nucleic acids described herein, once the mixture of nucleic acids is expressed in a cell, the phenotype of the physiological state can be replicated in a cell or a cellular process, thus allowing the skilled artisan to observe the phenotype transfer in a cell or cellular process.

Nucleic acid, preferably a transcriptome, may be obtained from any cell of interest in any physiological state. The donor cell may be any type of cell. A donor cell may be an eukaryotic cell or a prokaryotic cell. When the cell is an eukaryotic cell, the cell is preferably a mammalian cell, including but not limited to human, non-human primate, mouse, rabbit, rat, goat, guinea pig, horse cell, and the like. A non-mammalian eukaryotic cell includes a yeast cell, a plant cell, an insect cell, a protozoan cell and a fungal cell, including filamentous and non-filamentous fungi. When the cell is a prokaryotic cell the cell is a bacterial cell. Non-limiting examples of cells from which nucleic acid may be obtained include astrocytes, cardiomyocytes, neonatal cardiomyocytes, embryonic stem cells and neurons. RNA from any donor cell of interest can be phototransfected into any recipient cell in the method of the invention. Preferably, donor cells are of the same species as the recipient cells. Donor cells may be from the same individual as the recipient cell, or from a different individual. Donor cells may originate from the same germinal layer (e.g., ectoderm) as the recipient cell (e.g. both arise from ectoderm germ layer), or from a different germinal layer (e.g., one cell arises from ectoderm and the other arises from endoderm germ layer). Donor cells may be the same cell type as the recipient cell but at a different stage of differentiation, exposed to a candidate therapeutic, exposed to a toxin or pathogen, diseased. In yet other embodiments, a donor cell may be a recipient cell. For instance, nucleic acid from a donor cell is transferred into a first recipient cell. Nucleic acid from the first recipient cell is then subsequently transferred into a second recipient cell. In one aspect, the first and second recipient cells are in different physiological states. In another aspect, the first and second recipient cells are the same type of cell. As described elsewhere herein, RNA obtained from a cell may be used to transfect a cell, or may be used as a template to create cDNA. The cDNA may be used in in vitro transcription methods to amplify some or all of the RNA, which is then used in the method of the invention.

As a non-limiting example, the total RNA from a neuronal stem cell or other progenitor neuronal cell can be isolated from such a cell using techniques known in the art and disclosed elsewhere herein. To obtain an mRNA transcriptome, the total RNA can then be processed using various methods known in the art for isolating mRNA, such as isolation of mRNA using complementary poly-dT nucleic acids, which can be conjugated to beads or a column. The total mRNA obtained is then transfected into a recipient cell using the methods disclosed herein. The recipient cell then expresses the mixture of mRNA isolated from the neuronal stem cell and replicates the multigenic effect of the differential gene translation and regulation characteristic of a developing neuronal stem cell. The present invention is not limited to neuronal stem cells however, and can be used to determine the transferred multigenic phenotype of any type of developing or developed cell, provided that the total RNA and mRNA are isolated from the cell.

In one embodiment, total RNA or the mRNA transcriptome isolated from hair cells that respond to a particular frequency range (donor cells) can be isolated and transfected into a hair cell that responds to a different frequency range (recipient cells). In one aspect, the donor cell is a hair cell that responds to high frequencies. Exemplary high frequencies include about 15,000-20,000 Hz. Phenotypic responsiveness in the transfected cells can be assessed using morphological measurements (different frequency responders have different shapes) and/or physiological responsiveness such as electrophysiologic measurements and $Ca^{+2}$ influx. One of the major causes of age-related hearing loss is the loss of frequency responsive hair cells in the cochlea of the ear. Thus, this embodiment is contemplated to provide cells useful in the treatment for age-related hearing loss. Practice of this embodiment in vivo is further contemplated as treatment for age-related hearing loss.

As an alternative non-limiting example, the total RNA from a cell treated with a compound, such as a drug, a peptide, a cytokine, an antibody, a mitogen, a toxin, or other compounds known in the art, can be isolated using the methods disclosed herein and known in the art. The mRNA from that cell can then be transfected into another cell type using the methods disclosed herein, thus transferring the multigenic phenotype of the cell treated with a compound to another cell, thus enabling the rapid and specific determination of that compound on another cell type.

In another non-limiting embodiment of the present invention, the total RNA from a diseased cell, such as a tumor cell, a cell harboring an intracellular pathogen, a cell from a patient with an autoimmune disease, and the like, can be isolated from the diseased cell. The mRNA transcriptome from that cell can be isolated from the total RNA using, for example, poly-dT isolation techniques. The mRNA from the diseased cell is transfected into another cell using the methods of the present invention, thus transferring the multigenic phenotype of the diseased cell to another cell, providing a more accurate picture of the role interacting nucleic acids and their encoded proteins have in the phenotype of a cell.

As another non-limiting embodiment of the invention, the method of the invention can be practiced in order to prepare cells for testing therapeutics. Candidate therapeutics are typically tested on a number of different cell types, prior to assessment in animals or humans. These different cells often are cell lines that have a multiplicity of signaling pathways. The multiplicity of pathways may overlap and compensate for drug function and testing with regard to efficacy and/or side effects, thereby making assessment of the candidate drug effects less robust. According, it is contemplated that mRNA for one or more specified second messenger system pathways can be transfected into primary cells or cell lines of interest in order to create cells having enriched presence and/or activity of one or more pathways, thus these pathways will dominate over endogenous pathways. The mRNA are therefore a heterogenous collection of mRNAs that encode the various components for the one or more second messenger system pathways. Enriched presence and/or activity of one or more pathways is relative to a cell that has not had mRNA for one or more specified second messenger system pathways transfected into it. Candidate therapeutics can then be assessed for efficacy and/or side effects on the dominant pathways present in the cells with enriched expression of one or more specified second messenger system pathways. Non-limiting examples of second messenger systems include: the cAMP system; the phosphoinositol system; the arachidonic acid system; the cGMP system; and the tyrosine kinase system. It is expected that using such defined cell types permits improved assessment of the effect of a candidate on particular pathways. In one embodiment, modulation of endogenous pathways by decreasing expression of particular pathways is also contemplated. Modulation can be achieved by introducing siRNAs corresponding to mRNAs encoding particular proteins in a pathway into the cell to inhibit particular pathways. Such modulation can be performed simultaneously with the introduction of the mRNAs for the one or more specified second messenger system pathways, or can be done in one or more separate steps. In one embodiment, an embryonic fibroblast is used as the recipient cell. In one embodiment, the donor cells from which total RNA is obtained are cardiomyocytes and the recipient cell type is an embryonic fibroblast. In a preferred aspect, mRNA is extracted from the cardiomyocyte total RNA and is transfected into the embryonic fibroblast.

In another non-limiting embodiment, the method of the invention can be used to generate a knock out (KO) of one or more specific genes in a cell. The field of functional genomics has relied upon the generation of KO mice to elucidate the function of particular genes. The utility of KO mice has been enhanced by flanking a gene with FLOX-sites, which are recognized by CRE-recombinase. CRE-recombinase binds to FLOX-sites and removes the intervening sequence containing the gene, thereby knocking out that gene. Cell-type specific KO has been achieved by driving CRE-recombinase expression in particular cell types using cell-type specific promoters. Inducible promoters, such as TET-on or the ecdysone system, have been used to control the time of induction of CRE-recombinase expression; expression is induced upon exogenous addition of the cognate inducer. Advantageously, the method of the invention can be used to knock out a gene in a particular cell at a particular time without the use of inducible promoters and exogenous inducers. In one embodiment, mRNA encoding CRE-recombinase, or the protein itself, is transfected into cells having chromosomal material engineered genetically to contain FLOX sites flanking one or more genes of interest. The transfection can be done with a single engineered cell or with a population of the engineered cells. The method can also be practiced with live tissue samples or with a live animal. The method is not limited to the use of CRE-recombinase and FLOX sites. It can be practiced using any comparable system of specific sequence excision, such as zinc-finger nuclease technology and the FLP recombinase and FRT system. The method can also be used for targeted integration of a gene.

The present invention can further comprise the use of a nucleic acid from a cell or a population of cells of homogeneous or heterogeneous types. The present invention can further comprise the use of a nucleic acid, preferably mRNA, defined by the expression profile of a cell as determined using methods well known in the art, including, but not limited to, a gene array profile, total RNA, total mRNA, and the like. An expression profile is used to determine the relative abundances of mRNA in a cell. The expression profile is then used as a template to determine the relative abundances of mRNA in the physiological state of the cell from which the expression profile was made. A population of mRNA with the same relative abundance as in the cell for which expression has been profiled is produced using the methods disclosed elsewhere herein, including mRNA isolation, in vitro transcription or chemical synthesis. The resultant population of mRNA is then phototransfected into the cell using the methods described elsewhere herein, thereby transferring the phenotype of the cell from which the expression profile was made to another cell, tissue or animal.

In another embodiment, a population of mRNA reflecting the relative abundance of a cell in a particular physiological state further comprises mRNA encoding one or more polypeptides that facilitate phenotype conversion. For instance, the mRNA obtained from a neuronal cell may be supplemented with mRNA encoding proteins that stimulate exocytosis and is then phototransfected into a non-neuronal recipient cell.

The present invention may further comprises the sequential transfection, preferably sequential phototransfection, of a cell. Sequential transfection is used herein to refer to a process in which a cell is transfected at a first time point, and then transfected at a second or subsequent time point. As an example, a cell can be phototransfected on day 1, the result of which is that one or more nucleic acids are introduced into the cell. These nucleic acids can be expressed by the cellular translation complexes or remain silent, or can be inhibited using an inhibitory nucleic acid as disclosed elsewhere herein. On day 2, the same cell can be phototransfected again, transfecting one or more of the same or dissimilar nucleic acids to the same cell. The present invention is not limited to phototransfection separated by a day however. Sequential phototransfection can occur with minutes, hours, days, weeks or months between a first time point and a second time point, provided the phototransfection occurs to the same cell. Thus, the sequential phototransfection methods of the present invention are limited only by the lifespan of the cell. Another non-limiting example of sequential phototransfections comprises a first phototransfection on Day 1, a second phototransfection 48 hours later (Day 3) and a third phototransfection 7 days after the first phototransfection. The conditions of sequential transfection may be the same or different. The means of transfection may be changed and/or the number of sites transfected in a transfection step may be different among multiple transfections. For instance, the second and subsequent transfections using phototransfection may be performed using a reduced laser power compared to the laser power used in the first phototransfection.

The sequential phototransfection methods of the present application are useful for, among other things, analyzing temporal gene expression in a cell, analyzing the multigenic effects of a protracted developmental process, and determining the relationship of genotype to phenotype over the course of the viable life span of a cell. Sequential phototransfection using the same nucleic acids also increases the robustness of expression of the phototransfected nucleic acids. As shown herein, three sequential phototransfections of an astrocyte transcriptome into a neuron yields a durable phenotype conversion in a high percentage of neuron cells.

The embodiments of the inventions disclosed herein are not limited to mRNA. The present invention can further comprise reverse transcribing mRNA into cDNA, then transfecting the cDNA into a cell The present invention is not limited to the use of RNA and mRNA. A mixture of DNA and RNA can be used in the methods of the present invention to determine the effects of transient (RNA) as well as prolonged (DNA integration into the genome) gene expression in a cell.

When a mixture of nucleic acids, such as a mixture of RNAs is phototransfected into a cell, subpopulations of that mixture can be phototransfected into a cell to determine the core set of RNAs responsible for a given phenotype. As a non-limiting example, when the total RNA is isolated from a cell in a certain physiological state and mRNA is isolated from that population of total RNA, specific subpopulations of the isolated mRNA can be transfected into a cell to establish the core mRNAs responsible for that phenotype. The present embodiment can also be performed with cDNA produced from mRNA. Specific populations of mRNA can be identified using sequence homology data or other characteristic features known in the art and available from various databases, such as GenBank® (United States Department of Health and Human Services, Bethesda Md.).

Alternatively, the mRNA from a cell can be isolated and transfected into a cell using the methods of the present invention, and an siRNA, microRNA, antisense nucleic acid or ribozyme (collectively referred to as an inhibitory nucleic acid) can be transfected along with the mRNA, resulting in silencing and/or inhibition of an mRNA. Silencing an mRNA permits one of skill in the art to identify, for instance, the core mRNA(s) responsible for a multigenic phenotype. In addition, the present invention allows the replication of a phenotype in another cell without the step of determining the nucleic acid expression profile of a cell in a physiological state. The nucleic acid, preferably RNA, from a cell in a specific physiological state, such as a certain differential or disease state, can be isolated. Preferably, an mRNA transcriptome is then isolated. Using the methods of the present invention, the RNA, or a cDNA of the RNA, can be transfected into a cell in order to analyze the phenotype in the transfected cell once the nucleic acid has been expressed. The nucleic acid, preferably RNA, can be the total RNA from a cell, or a subpopulation of the RNA, such as the mRNA transcriptome.

To assess the effect of expression of the transfected nucleic acids, cells transfected in accordance with the method of the invention can be examined using methods known in the art. Assessments may be made, for example, of phenotypic changes, mRNA expression, protein expression and functional assays. Examples of such analyses include, but are not limited to, cell morphology, presence and absence of immunological markers, RT-PCR, expression profiling, mRNA abundance measurements, immunocytochemistry analysis (ICC) for specific proteins, cell viability, and cell-specific activities, such as cell division-mitosis and electrophysiology.

Optionally, the present method further comprises inhibiting transcription factors in the transfected cell, thus preventing competition between expression of endogenous and exogenous mRNAs and the proteins encoded thereby. A transcription factor can be inhibited by addition of exogenous agents, such as an inhibitory nucleic acid or compounds that inhibit transcription factors, such as a protease, or SP100030 (Huang et al., 2001, Br. J. Pharmacol., 134: 1029-1036). Other agents useful for inhibiting transcription in a recipient cell include, but are not limited to, α-amanitin, trichostatin A (TSA; a histone deacetylase inhibitor), tubulin depolymerizer and actin depolymerizer. Preferably, a recipient cell is contacted with one or more transcription inhibition agents prior to transfection. Preferably, the cell is contacted between about 30 minutes and about 80 hours, preferably between about 30 minutes and about 60 hours and more preferably, between about 6 hours to about 48 hours, prior to transfection. In a non-limiting example, a rat hippocampal neuron is contacted with TSA and α-amanitin at a final concentration of 100 nM and 100 microgram per ml in a neuronal cell medium, respectively. The neuron is then irradiated between about 24 to about 55 hours later. In some embodiments of the invention including sequential phototransfection of a recipient cell, the recipient cell is preferably not contacted with a transcription inhibitor subsequent to the first phototransfection.

As shown herein, durable phenotype conversion is achievable without inhibition of transcription factors. Accordingly, in a preferred embodiment, the methods of the invention are practiced in the absence of exogenous agents for transcription factor inhibition. "Exogenous agent" in this context excludes any inhibitors encoded by a transcriptome or present in the transcriptome from the donor cell.

FIG. 1A depicts a non-limiting example of a timeline for phototransfection of a recipient cell, for instance a neuron, with phenotype-converting nucleic acid, such as the mRNA transcriptome from a donor cell, for instance, a glial cell. The timeline depicts three sequential phototransfections in the complete absence of transcription inhibitor treatment, followed by a period of phototransfection cell recovery and a period of cell remodeling and redifferentiation. A possible change in growth media from a recipient-cell-specific medium to a donor-cell-specific medium is indicated after the first phototransfection. Such media changes are useful, for instance, for supporting phenotype conversion. Assays that may be used to characterize the remodeling and redifferentiation of the phototransfected recipient cell are enumerated in the box on the top right.

The present method can also be used for the specific and local transfection of an inhibitory nucleic acid, such as an siRNA, antisense nucleic acid or a microRNA (miRNA), using the methods of the present invention. Using the invention disclosed herein, the skilled artisan can specifically inhibit a cellular nuclear acid, especially those in cellular processes. Further, as disclosed elsewhere herein, an inhibitory nucleic acid can be used to identify the core nucleic acid(s) involved in a multigenic phenotype.

The phenotype-converting nucleic acids useful in the methods of the present invention may comprise a variety of nucleic acids, including various species of RNA (mRNA, siRNA, miRNA, hnRNA, tRNA, total RNA, combinations thereof and the like) as well as DNA. Methods for isolating RNA from a cell, synthesizing a short polynucleotide, constructing a vector comprising a DNA insert, and other methods of obtaining a nucleic acid to phototransfect into a cell are well known in the art and include, for example, RNA isolation, cDNA synthesis, in vitro transcription, and the like.

The nucleic acid compositions of this invention, whether RNA, cDNA, genomic DNA, or a hybrid of the various combinations, may be isolated from natural sources or may be synthesized in vitro. Techniques for nucleic acid manipulation are described generally in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York)., incorporated herein by reference. Nucleic acids suitable for use in the present method also include nucleic acid analogs. Examples of such analogs include, but are not limited to, phosphorothioate, phosphotriester, methyl phosphonate, short chain alkyl or cycloalkyl intersugar linkages, or short chain heteroatomic or heterocyclic intersugar ("backbone") linkages. In addition, nucleic acids having morpholino backbone structures (U.S. Pat. No. 5,034,506) or polyamide backbone structures (Nielsen et al., 1991, Science 254: 1497) may also be used.

The methods of the present invention can comprise the use of a variety of nucleic acids, including DNA, RNA, a cDNA reverse transcribed from an mRNA, an RNA transcribed from that cDNA, a DNA amplified from the cDNA, an RNA transcribed from the amplified DNA, and the like. The present invention further comprises using single-stranded and double-stranded RNA and DNA molecules. Any coding sequence of interest can be used in the methods of introducing and translating a nucleic acid in a cell or in a cellular process, such as a dendrite. One of skill in the art will understand, when armed with the present disclosure, that a multitude of properties of a cellular process, and by association, of the attached cell, can be affected by the methods of the present invention. For instance, for studies of dendrite remodeling, any coding sequence for a protein involved in the growth, homeostasis or remodeling of a dendrite are useful in the methods of the invention. Non-limiting examples of such proteins include: cadherin, neurexin, synaptophysin, tubulin, microtubule associated proteins and actin.

In one embodiment of the present invention, the nucleic acid phototransfected into a cell is all or a portion of the total mRNA isolated from a biological sample. The term "biological sample," as used herein, refers to a sample obtained from an organism or from components (e.g., organs, tissues or cells) of an organism. The sample may be of any biological tissue or fluid. The nucleic acid (either genomic DNA or mRNA) may be isolated from the sample according to any of a number of methods well known to those of skill in the art.

Methods of isolating total mRNA are well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993)).

Preferably, the total nucleic acid is isolated from a given sample using, for example, an acid guanidinium-phenol-chloroform extraction method and polyA$^+$ mRNA is isolated by oligo dT column chromatography or by using (dT)n magnetic beads. Commercially available products, such as TRIZOL and MICRO-FASTTRACK (Invitrogen™, Carlsbad, Calif.), are useful in extracting nucleic acid from a biological sample.

The mRNA can be locally transfected directly into a cell or a cellular process, or the sample mRNA can be reverse transcribed with a reverse transcriptase and a promoter comprising an oligo dT and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, supra.; Van Gelder, et al., 1990, Proc. Natl. Acad. Sci. USA, 87: 1663-1667). Moreover, Eberwine et al. (1992, Proc. Natl. Acad. Sci. USA, 89: 3010-3014) provide a protocol using two rounds of amplification via in vitro transcription to achieve greater than $10^6$ fold amplification of the original starting material.

The present invention further comprises the use of in vitro transcription for phototransfection into a cell or cellular process. In vitro transcription comprises the production of dsRNA by transcribing a nucleic acid (DNA) segment in both directions. For example, the HiScribe™ RNAi transcription kit (New England Biolabs, Ipswich, Mass.) provides a vector and a method for producing a dsRNA for a nucleic acid segment that is cloned into the vector at a position flanked on either side by a T7 promoter. Separate templates are generated for T7 transcription of the two complementary strands for the dsRNA. The templates are transcribed in vitro by addition of T7 RNA polymerase and dsRNA is produced. Similar methods using PCR and/or other RNA polymerases (e.g., T3 or SP6 polymerase) can also be used and are known in the art.

The present invention further comprises the use of chemically synthesized nucleic acids for use in phototransfection. Oligonucleotides for use as probes can be chemically synthesized according to the solid phase phosphoramidite triester method first described by Beaucage, (1981, Tetrahedron Letts., 22:1859-1862) using an automated synthesizer, as described in Needham-VanDevanter, et al. (1984, Nucleic Acids Res., 12:6159-6168). Purification of oligonucleotides is by either native acrylamide gel electrophoresis or by anion-exchange HPLC as described in Pearson (1983, J. Chrom., 255:137-149). The sequence of the synthetic oligonucleotides can be verified using the chemical degradation method of Maxam (1980, in Grossman and Moldave, eds., Methods in Enzymology, Academic Press, New York, 65:499-560).

The present invention can further comprise the use of DNA in a process to locally transfect a cell or a cellular process via phototransfection. The DNA can be contained in a vector, such as those described herein.

The invention includes an isolated DNA encoding a protein operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Expression of a protein in a cell or a cellular process phototransfected as disclosed herein may be accomplished by generating a plasmid or other type of vector comprising the desired nucleic acid operably linked to a promoter/regulatory sequence which serves to drive expression of the protein, with or without a tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, as well as the Rous sarcoma virus promoter, and the like. Moreover, inducible and tissue specific expression of the nucleic acid encoding a protein can be accomplished by placing the nucleic acid encoding a protein under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Selection of any particular plasmid vector or other DNA vector is not a limiting factor in this invention and a wide plethora of vectors are well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The nucleic acids encoding a protein can be cloned into various plasmid vectors. However, the present invention should not be construed to be limited to plasmids or to any particular vector. Instead, the present invention should be construed to encompass a wide plethora of vectors which are readily available and/or well-known in the art.

The present invention further comprises locally transfecting an inhibitory nucleic acid, such as an antisense nucleic acid, an siRNA or an miRNA via phototransfection into a cell. An siRNA polynucleotide is an RNA nucleic acid molecule that interferes with RNA activity that is generally considered to occur via a post-transcriptional gene silencing mechanism. An siRNA polynucleotide preferably comprises a double-stranded RNA (dsRNA) but is not intended to be so limited and may comprise a single-stranded RNA (see, e.g., Martinez et al., 2002, Cell 110:563-74). The siRNA polynucleotide included in the invention may comprise other naturally occurring, recombinant, or synthetic single-stranded or double-stranded polymers of nucleotides (ribonucleotides or deoxyribonucleotides or a combination of both) and/or nucleotide analogues as provided herein (e.g., an oligonucleotide or polynucleotide or the like, typically in 5' to 3' phosphodiester linkage). Accordingly it will be appreciated that certain exemplary sequences disclosed herein as DNA sequences capable of directing the transcription of the siRNA polynucleotides are also intended to describe the corresponding RNA sequences and their complements, given the well established principles of complementary nucleotide base-pairing.

An siRNA may be transcribed using as a template a DNA (genomic, cDNA, or synthetic) that contains a promoter for an RNA polymerase promoter. For example, the promoter can be the U6 promoter or the H1 RNA polymerase III promoter. Alternatively, the siRNA may be a synthetically derived RNA molecule. In certain embodiments, the siRNA polynucleotide may have blunt ends. In certain other embodiments, at least one strand of the siRNA polynucleotide has at least one, and preferably two nucleotides that "overhang" (i.e., that do not base pair with a complementary base in the opposing strand) at the 3' end of either strand of the siRNA polynucleotide. In a preferred embodiment of the invention, each strand of the siRNA polynucleotide duplex has a two-nucleotide overhang at the 3' end. The two-nucleotide overhang is preferably a thymidine dinucleotide (TT) but may also comprise other bases, for example, a TC dinucleotide or a TG dinucleotide, or any other dinucleotide. The overhang dinucleotide may also be complementary to the two nucleotides at the 5' end of the sequence of the polynucleotide that is targeted for interference. For a discussion of 3' ends of siRNA polynucleotides see, e.g., WO 01/75164.

Preferred siRNA polynucleotides comprise double-stranded polynucleotides of about 18-30 nucleotide base pairs, preferably about 18, about 19, about 20, about 21, about 22, about 23, about 24, about 25, about 26, or about 27 base pairs, and in other preferred embodiments about 19, about 20, about 21, about 22 or about 23 base pairs, or about 27 base pairs. The siRNA polynucleotide useful in the present invention may also comprise a polynucleotide sequence that exhibits variability by differing (e.g., by nucleotide substitution, including transition or transversion) at one, two, three or four nucleotides from a particular sequence. These differences can occur at any of the nucleotide positions of a particular siRNA polynucleotide sequence, depending on the length of the molecule, whether situated in a sense or in an antisense strand of the double-stranded polynucleotide. The nucleotide difference may be found on one strand of a double-stranded polynucleotide, where the complementary nucleotide with which the substitute nucleotide would typically form hydrogen bond base pairing, may not necessarily be correspondingly substituted. In preferred embodiments, the siRNA polynucleotides are homogeneous with respect to a specific nucleotide sequence.

Polynucleotides that comprise the siRNA polynucleotides may in certain embodiments be derived from a single-stranded polynucleotide that comprises a single-stranded oligonucleotide fragment (e.g., of about 18-30 nucleotides) and its reverse complement, typically separated by a spacer sequence. According to certain such embodiments, cleavage of the spacer provides the single-stranded oligonucleotide fragment and its reverse complement, such that they may anneal to form, optionally with additional processing steps that may result in addition or removal of one, two, three or more nucleotides from the 3' end and/or the 5' end of either or both strands, the double-stranded siRNA polynucleotide of the present invention. In certain embodiments the spacer is of a length that permits the fragment and its reverse complement to anneal and form a double-stranded structure (e.g., like a hairpin polynucleotide) prior to cleavage of the spacer, and optionally, subsequent processing steps that may result in addition or removal of one, two, three, four, or more nucleotides from the 3' end and/or the 5' end of either or both strands. A spacer sequence may therefore be any polynucleotide sequence as provided herein that is situated between two complementary polynucleotide sequence regions which, when annealed into a double-stranded nucleic acid, result in an siRNA polynucleotide.

The present method further comprises methods for introducing a nucleic acid into a cell. The method comprises phototransfecting a cell in the presence of a nucleic acid, preferably RNA and/or DNA, where the nucleic acid is in a fluid medium permitting the transfer of the nucleic acid from one side of the cell membrane to the other side of the cell membrane through a hole in the cell membrane. The fluid medium can comprise any medium having the buffering capacity and pH to support the viability of a cell and the stability of a nucleic acid molecule. Contemplated media include, but are not limited to, phosphate buffered saline, Tris, Tris-EDTA (TE) cell culture media, other aqueous mediums and buffers, and the like.

The number of nucleic acid molecules that enter the cell is influenced by the nucleic acid concentration in the nucleic acid bath, the size of the nucleic acid molecule, and laser intensity, e.g., the length of each laser pulse and the number of laser pulses delivered. Based on the teachings herein, the skilled artisan can readily adjust the parameters of the phototransfection process to control the approximate number of nucleic molecules that enter the neuron per pulse.

In one embodiment, a cell is surrounded by an nucleic acid bath comprising a nucleic acid molecule, preferably an RNA molecule, at about 1 to about 150 µg/ml, more preferably about 10 to about 100 µg/ml, and more preferably still at about 10 to about 50 µg/ml in the bath. Preferably the bath is in a container that is permeable by a laser and does not distort the beam, even more preferably, the bath is optically clear glass with a thickness of about 0.1 mm.

In another embodiment, a cell is bathed in discrete locations on the cell surface with a solution comprising a nucleic acid molecule. For instance, using a patch pipette, micropipette or other applicator, a solution comprising nucleic acid is applied to a discrete location on the surface of a cell. The solution may be applied to more than one location on a cell. The cell is then irradiated using a laser at one or more sites within a discrete location. Nucleic acid in the solution is present at about 1 nanogram per microliter (ng/µl) to about 2 microgram/microliter (µg/µl), preferably about 50 ng/µl to about 1 µg/µl, and more preferably about 100 ng/µl to about 500 ng/µl.

The present invention further comprises the use of other methods for introducing a nucleic acid to a cell, tissue or animal via phototransfection. Methods included in the present invention include, for example, perfusion, picospritzing, microinjection and the like. Methods for perfusion include, but are not limited to, using a pump to move a fluid medium comprising a nucleic acid, preferably RNA, even more preferably mRNA, to a cell, tissue or animal. The fluid medium used in the perfusion methods of the present invention can included those disclosed elsewhere herein, such as buffered solutions that support and maintain the stability of a nucleic acid and a cell, tissue or animal. In one embodiment of the present invention, the fluid medium can include a medium, such as Basal Media Eagle (BME), BGJb Medium, Brinster's BMOC-3 Medium, CMRL Medium, CO$_2$-Independent Medium, Dulbecco's Modified Eagle Media (D-MEM), F-10 Nutrient Mixtures, F-12 Nutrient Mixtures, Glasgow Minimum Essential Media, Grace's Insect Cell Culture Media, Improved MEM, IPL-41 Insect Media, Iscove's Modified Dulbecco's Media, Leibovitz's L-15 Media, McCoy's 5A Media (modified), MCDB 131 Medium, Media 199, Medium NCTC-109, Minimum Essential Media (MEM), Modified Eagle Medium (MEM), Opti-MEM® I Reduced Serum Media, RPMI Media 1640, Schneider's Drosophila Medium, Waymouth's MB 752/1 Media, Williams Media E, artificial spinal fluid (aCSF), Ringer's solution and the like. The present invention can further comprise the use of buffered salt solutions, including, but not limited to, Dulbecco's Phosphate-Buffered Saline (D-PBS), Earle's Balanced Salt Solution, Hanks' Balanced Salt Solution, Phosphate-Buffered Saline (PBS), and the like.

The present invention further comprises using picospritzing in conjunction with phototransfection to introduce a nucleic acid to a cell, organ or tissue. Picospritzing comprises the use of electrical pulses with a pressure device to deliver a compound, such as a nucleic acid, to a cell, tissue or animal. Method for picospritzing are known in the art and are described in, for example, Herberholz, et al., 2002, J. Neuroscience, 22: 9078-9085). Picospritzing apparatuses are available from, for example, World Precision Instruments (Sarasota, Fla.).

In another embodiment, transfection of cells with nucleic acids encoding two or more different polypeptides is effected by microinjection. In these embodiments, the recipient cell is preferably a somatic cell, preferably a somatic, differentiated cell.

The present invention comprises irradiating a cell with a laser to phototransfect and locally transfect the cell. When the laser contacts the cell membrane, or cell wall in the case of plant cells, fungal cells, and other cells comprising a cell wall, the plasma membrane or cell wall is perforated, permitting the diffusion of foreign molecule, such as RNA and/or DNA, to enter the cell. The fluidity of mammalian cell membranes facilitates subsequent closure of the perforation. Lasers compatible with the present invention include, but are not limited to, continuous-wave argon-ion lasers operating at 488 nm (Schneckenburger, et al., 2002, J. Biomed. Opt., 7: 410-416; Palumbo et al., 1996, J. Photochem. Photobiol. B-Biol., 36: 41-46), pulsed and frequency upconverted Nd:YAG lasers operating at 355 nm (Shirahata, et al., 2001, J. Invest. Med., 49: 184-190), 532 nm (Soughayer, et al., 2000, Anal. Chem., 72: 1342-1347), and 1064 nm (Mohanty, et al., 2003, Biotechnol. Lett. 25: 895-899), and femtosecond titanium-sapphire lasers (Tirlapur, et al., 2002, Plant J. 31: 365-374; Tirlapur, et al., 2002, Nature 418: 290-291; Zeira, et al., 2003, Mol. Therapy. 8: 342-350). Preferably, a titanium-sapphire laser at 405 nm (PicoQuant GmbH, Berlin Germany) is used to phototransfect a cell. However, the present invention is not limited to the a titanium-sapphire laser, but includes any laser with the capacity of delivering a localized focal volume of about $10^{-19}$ m$^3$.

Control of the incident laser beam is achieved by using various apparatuses to control the focus and power of the laser, as well as to aim the laser. Focusing the laser is achieved by passing the incident laser through a lens, such as a microscope lens, placed between the laser and the cell. The power of the laser in controlled by modulating the voltage and current going to the laser and through the use of neutral density filters or pockels cells. Exposure of the cells to the laser is controlled through a shutter, such as a single lens reflex (SLR) camera shutter and/or with electronically controlled pockels cells.

Aiming the laser is accomplished through a microscope lens and with dielectric and steering mirrors and AOD (acoustic optical deflector) between the laser source and a cell. A microscope useful in the practice of the present invention includes, but is not limited to, a confocal microscope, a multiphoton excitation fluorescence microscope, a light microscope, and the like. The present method further comprises aiming the laser using an optical fiber to transmit the laser to a distant or difficult-to-access area. As a non-limiting example, an optical fiber is used to phototransfect intestinal, neural or cardiothoracic cells in a live animal. Further, the present invention comprises phototransfecting a cell or a population of cells using multiple optical fibers in an animal. Optical fibers are well known in the art and are described in, for example, U.S. Pat. Nos. 3,711,262 6,973, 245.

A laser beam with less than a milliwatt of power for tens of milliseconds is sufficient to porate a cell (Paterson, et al., 2005, Optics Express, 13: 595-600). Preferably, the laser has a power density of about 1200 MWm$^{-2}$ and a total power of about 30-55 mW at the back aperture of the lens. Further, in order to provide maximum surface area for transfection, the laser beam should be highly circular (dx=dy) with beam diameter of about 2 mm.

The starting power output of the laser is attenuated through the use of various filters, such as a neutral density (ND) filter to reduce the power to the milliwatt range required for phototransfection with no attendant pathological effects on the target cell. The beam can be expanded through the used of a telescope where f=100 mm, and directed into a microscope, such as a light microscope or an oil-immersion microscope with a ×100 objective (N.A.=1.25). An SLR shutter between the laser source and the microscope permits control of the exposure time. An exposure time of about 40 ms is sufficient to porate a cell without attendant damage, but this parameter can be altered to increase or decrease exposure time.

Target cells in a nucleic acid bath are positioned and focused on by manipulating the stage of the microscope and/or using dielectric and steering mirrors and AOD, so the beam is focused on the cell membrane and not towards the nucleus of the cell. When porating a cellular process, such as a dendrite, the beam is focused directly on the cellular process.

An exemplary phototransfection protocol comprises at least two and preferably three sequential phototransfection steps of a recipient cell using the transcriptome, preferably the mRNA transcriptome, from a donor cell. The mRNA transcriptome comprises a range of mRNA sizes and has an average transcript size between about 1 to 3.5 kb. The first phototransfection step is at about 35 mW using a titanium-sapphire laser and subsequent phototransfections steps are at a lower power, such as 30 mW or less. Each phototransfection step involves laser irradiating the recipient cell at numerous, random sites. The number of sites per step is determined by consideration of the strength of the laser, the diameter of the pores that result in the irradiated site, the average size of the transcripts in the mRNA transcriptome and modeling transport of individual transcripts through the pore using Brownian dynamics. After the first phototransfection step, the recipient cell may be transferred to a growth medium specific for the donor cell.

The cell or cellular process is irradiated with a laser according to the parameters disclosed herein. In one embodiment, the cells are transfected with a nucleic acid comprising a marker that indicates a successful transfection. Such markers are known in the art and include, for example, antibiotic resistance and fluorescent proteins. Successful poration can be tracked by the addition of a detectable molecule to the nucleic acid solution. Such molecules are well known in the art. Preferably, the molecule is non-toxic to the recipient cell. Non-limiting examples include Lucifer yellow and carboxyfluorescein diacetate succinimidyl ester. The cells are incubated according to the incubation conditions prior to irradiation with the laser. Expression of the locally transfected nucleic acid is analyzed according to the presence and activity of a marker or the phenotype of the cell.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods used in Experimental Examples 1-6 below are now described.

RNA Isolation, Amplification and Array Analysis:

Rat astrocytic transcriptome was extracted from the astrocyte culture using TRIzol® Reagent and Micro-FastTrack™ 2.0 Kit. The host hippocampal culture was prepared as previously described (Fukaya, et al. (2007) Arachidonic acid preserves hippocampal neuron membrane fluidity in senescent rats. *Neurobiol Aging* 28(8):1179-1186; Neufeld et al., (1985) Uptake and subcellular distribution of [3H]arachidonic acid in murine fibrosarcoma cells measured by electron microscope autoradiography. *J Cell Biol* 101(2):573-581). After TIPeR, some coverslips were assessed using standard calcium imaging and immunocytochemistry methods. The rest of the samples were assessed using standard single-cell harvesting and aRNA amplification methods as previously described (Van Gelder et al., (1990) Amplified RNA synthesized from limited quantities of heterogeneous cDNA. *Proceedings of the National Academy of Sciences of the United States of America* 87 (5), 1663; Eberwine, et al., (2001) Analysis of mRNA populations from single live and fixed cells of the central nervous system. *Current protocols in neuroscience/editorial board*, Jacqueline N. Crawley et al Chapter 5, Unit 5 3; and Eberwine, (2001) Single Cell Molecular Biology *Nat Neurosci* 4 Suppl, 1155-1156). For the final aRNA synthesis, the Ambion Illumina TotalPrep RNA Amp kit was used, with an incubation time of 14 hours. The aRNA obtained from individual TIPeRed cells was used for nested RT-PCR to detect the expression of GFAP and MAP2, and for Affymetrix Rat 230 2.0 analysis where a volume of 40 ul, containing 2 ug of aRNA.

Modeling Phototransfection Procedure:

The laser excitation pulse was assumed to form a transient permeability of the membrane, where the permeability had an exponential decay (t). A distribution of membrane pore sizes was assumed to form in the area of laser excitation (250 nm diameter of laser excitation), and the spot of excitation was moved in a random positional sequence, identical to the phototransfection process. Across 16 separate regions of the plasma membrane, the phototransfection pulse produced a population of pores within the plasma membrane that would permit the transfer of dyes/mRNAs from the extracellular compartment to the cytosol. Although the exact pore size was not known, it was assumed that the distribution of pore sizes was Gaussian, with separate simulations evaluating transport across the plasma membrane for average pore sizes of 10 nm, 50 nm, 75 nm, and 125 nm radius, based on estimates for stable pore sizes ranging from 1 nm-250 nm. Transport of individual transcripts through the pore was modeled using Brownian dynamics, accounting for the steric interaction of the transcript with the pore by adjusting the free diffusivity of the transcript accordingly. Both entry and exit of the transcript was accounted for by simulating molecular positions with 1 microsecond timesteps.

Phototransfection:

A multiphoton scanhead attached to an Olympus BX61 fixed-stage upright microscope equipped with a water-immersed 40× lens (LUMPlanFI/IR, numerical aperture (NA) 0.8) to monitor and mediate the phototransfection process. Two sets of galvanometer-controlled mirrors were used independently for simultaneous imaging and phototransfecting. A transmitted light gradient contrast image was taken when the targeted neuron (DIV1) was found and the phototransfected area was selected and outlined. A micropippette was backfilled with RNAs (200 ng/ul) mixed with Lucifer yellow (LY) dye (Sigma, final concentration 0.5 mM). The RNA mixture was ejected to the neuron using a Nanoject II tool (Drummond Scientific Company). Once the Lucifer Yellow dye reached the maximal saturation, indicating the highest RNA concentration surrounding the neuron, phototransfection was started using the titanium-sapphire laser (Mai-Tai, Spectral Physics). The titanium-sapphire laser created 16 random transient poration sites within the outlined area by delivering laser pulses (~100 femtosecond, ~100 MHz) for 5 ms at a power of 35 mW (at the back aperture of the lens). The laser pulses were moved randomly over the 16 sites with 5 ms interval between each pulse, which allowed the RNA mixture to diffuse into the targeted neuron through these transient holes. The second and third phototransfection were performed 48 hours and 7 days later, following the same procedure as described above, but with lower laser power (30 mW at the back aperture of the lens).

After phototransfection the cells were cultured in astrocyte medium supplemented with arachidonic acid and Dharmafect3 to bolster host cell lipid composition during the TIPeR-induced remodeling of cellular phenotype (Fukaya T, et al. (2007) Arachidonic acid preserves hippocampal neuron membrane fluidity in senescent rats. *Neurobiol Aging* 28(8):1179-1186; Neufeld E J, Majerus P W, Krueger C M, & Saffitz J E (1985) Uptake and subcellular distribution of [3H]arachidonic acid in murine fibrosarcoma cells measured by electron microscope autoradiography. *J Cell Biol* 101(2): 573-581).

Immunocytochemistry:

Coverslips with cultured cells were fixed using 4% paraformaldehyde, then permeabilized using 0.2% triton-X for 15 min at room temperature. Endogenous biotin was blocked using the endogenous biotin blocking kit (Molecular Probe). Cells were blocked in 10% normal goat serum and 3% BSA for 1 hour at 37° C. Coverslips were then incubated using a mouse antibody against GFAP (1:250, Abcam) for 1 hour at 37° C., followed by incubation with goat anti-mouse secondary antibody conjugated with Alexa 546 (1:500, Molecular Probe) for 8 minutes at 37° C. Coverslips were again immunolabeled using a mouse antibody against NeuN (1:50, Abcam) for 1 hour at 37° C., followed by incubation with goat anti-mouse secondary antibody conjugated with Alexa 488 (1:500, Molecular Probes) for 8 minutes at 37° C. Lastly, fibronectin immunoreactivity was detected using a rabbit antibody against fibronectin (1:250, Abcam) for 1 hour at 37° C., followed by incubation with goat anti-rabbit secondary antibody conjugated with Alexa 647 (1:500, Molecular Probe) for 8 minutes at 37° C. Coverslips were finally mounted using Vectashield with DAPI (Vector Labs). Expression of GFAP, NeuN and fibronectin was detected using a confocal microscope (LSM 510, Carl Zeiss).

Calcium Imaging:

Calcium imaging was performed on an Olympus Fluoview FV1000 unit with an IX81 motorized inverted confocal microscope using a 20× lens (0.7 NA) at room temperature. Cells were loaded with Fluo-4AM (10 µM, Sigma) for 50 minutes at room temperature. Intracellular calcium changes were constantly imaged in 3-second intervals throughout. For analysis, region of interest were selected based on reference DIC image of cells, which were taken during the TIPeR procedure, over gridded coverslips. Background subtracted fluorescent signal intensity (ΔF/F) was used to evaluate physiological responses. Due to the low level of signal intensity, 5 consecutive images were integrated for analysis. The threshold for responses was set for 5% of changes and compared to the signals before and during drug applications. Image processing was performed using MetaMorph and Sigmaplot.

Single Cell Nested RT-PCR:

Primer sequences used for PCR (listed in order of forward primer and reverse primer) included:

```
GFAP outer (SEQ ID No. 1:
5'-AGTGGCCACCAGTAACATGCAA-3';

SEQ ID No. 2:
5'-TTGTCTTGCTCCAGCAGCCTAT-3')
and

GFAP inner (SEQ ID No. 3:
5'-AGAAACCAGCCTGGACACCAAA-3';

SEQ ID No. 4:
5'-TGGGAATTGGGCCTAGCAAACA-3'),
and

MAP2 outer (SEQ ID No. 5:
5'-ATGGCCACCAAGACCTTGGAAA-3';

SEQ ID No. 6:
5'-ACGGACTTTGTCATCGGTTCCT-3')
and

MAP2 inner (SEQ ID No. 7:
5'-TGGAGGGCAAACTACCCAAGTT-3';

SEQ ID No. 8:
5'-ATCAGCAACAGGTGGCAAACCA-3').
```

For the templates, cDNAs for each sample were synthesized using 1 µl of third-round aRNAs with random hexamer and SuperScript III reverse transcriptase (Invitrogen). A total number of 45 cycles of amplification was used with an annealing temperature at 57° C. (first round) and at 60° C. (second round). The final PCR products were examined using 2% agarose gel electrophoresis and then cloned into pCR2.1-TOPO vector using TOPO® TA Cloning Kit (Invitrogen). Sequences of the cloned PCR products were determined against nr nucleotide database at the NCBI website using BLAST search algorithm.

Computational Analysis of Single-Cell Transcriptome:

Analysis involved several aspects: i) transcriptome quantification; ii) bootstrap cluster analysis; iii) delineation of gene sets of biological interest; iv) visualization of transcriptome space; and v) Trans-activation of genes by donor astrocyte RNA.

i) Transcriptome Quantification.

For each single-cell transcriptome microarray measurements, probes with pervasive low quality measurements were removed (as reported by Affymetrix MAS 5.0) for all samples, in order to account for both background expression variability. Genes related to the phototransfection effect were also removed, by selecting genes that differentiate the N-TIPeR-N cells from the neurons (using Welch's t-test). Probe set expression intensities were background corrected using the Robust Multichip Average algorithm (Bolstad B M I R, Astrand M, Speed T P (2003) A comparison of normalization methods for high density oligonucleotide array data based on variance and bias. *Bioinformatics*), quantile normalized, and summarized using an upper-decile statistic, as implemented in the Bioconductor package affyPLM (Gentleman R C, et al. (2004) Bioconductor: open software development for computational biology and bioinformatics. *Genome Biol* 5 (10):R80; Bolstad BM IR, Astrand M, Speed TP (2003) A comparison of normalization methods for high density oligonucleotide array data based on variance and bias. *Bioinformatics*). The quality control resulted in 3104 most informative genes for characterizing the cells.

ii) Bootstrap Cluster Analysis.

The single-cell transcriptome was clustered based on the Euclidean distances between their expression profiles using the standard Unweighted Pair Group Method with Arithmetic mean (UPGMA) clustering method. To assess the robustness of the clusters, a set of 1000 bootstrap datasets were generated by resampling the 3104 informative genes with replacement, recomputing a UPGMA cluster tree for each and then computing a consensus tree using PHYLIP (Felsenstein J (Phylogeny Inference package Seattle), 3.6). For each cluster in the consensus tree, the number of times that each putative cluster was found in the 1000 re-sampled data sets was counted.

iii) Delineating Gene Sets of Biological Interest.

Within our informative set of 3104 genes, different gene sets of biological interest were isolated by contrasting astrocytes against neurons. Gene sets that best discriminate a biological contrast of interest were identified by performing a Welch's t-test for each gene and extracting top 10% significantly differentially expressed genes with at least a two-fold average expression differential. Gene sets that contrast the following biological conditions were extracted: astrocyte vs neurons (630 genes); astrocyte vs astro-TIPeR (136 genes); neurons vs astro-TIPeR (43 genes); and astro-TIPeR vs neuro-TIPeR (560 genes). We also generated A set of significantly similar gene groups between different cell types was generated using top 10% similar genes with the Welch's t-test statistic: astrocyte equals astro-TIPeR (69 genes); neuron equals astro-TIPeR (46 genes); and astro-TIPeR equals neuro-TIPeR (370 genes).

iv) Visualizing Transcriptome Space.

To generate each axis shown

Figure 4A:
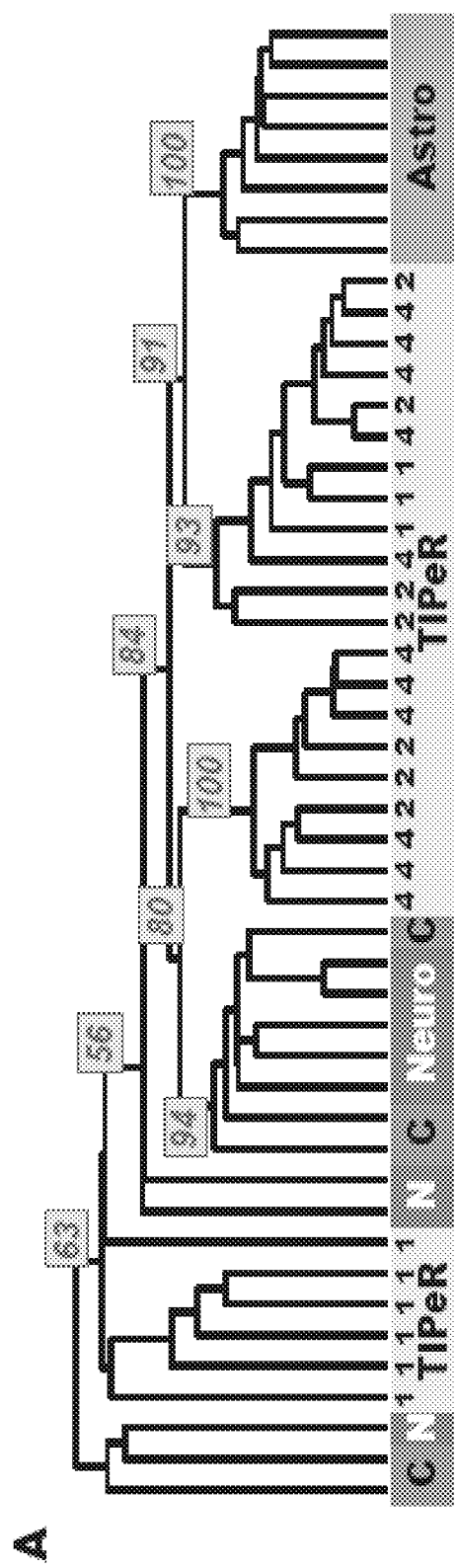
Figure 4B:
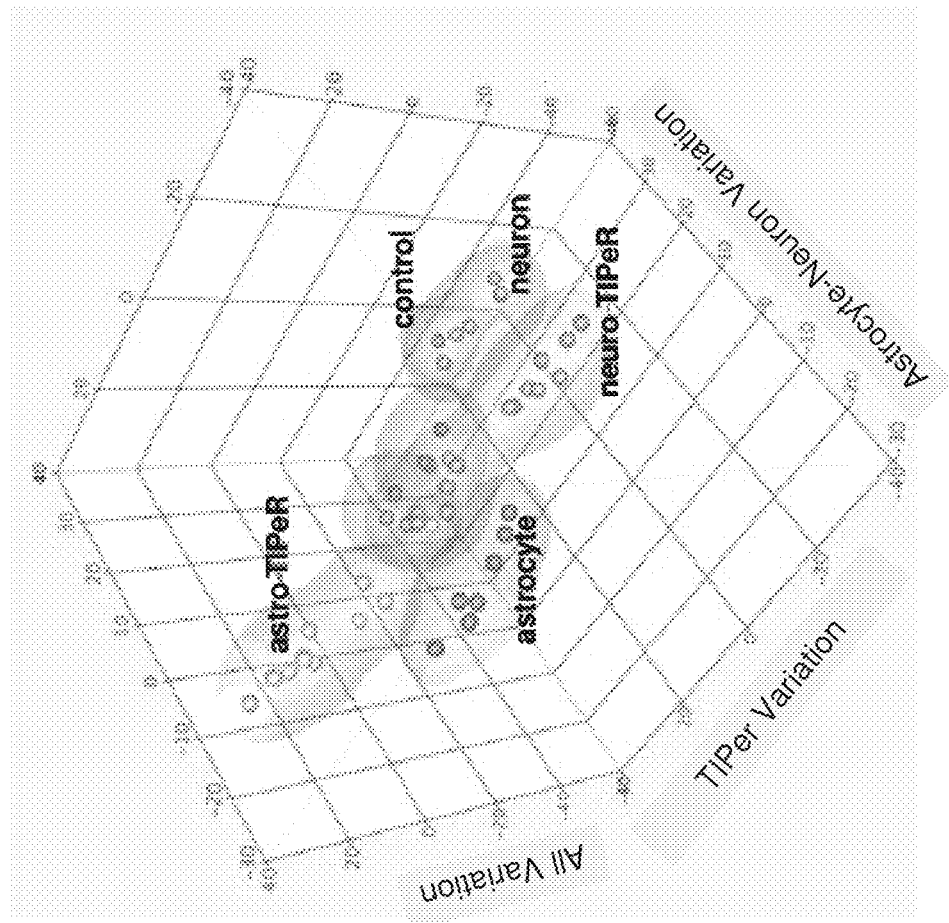

FIG. 4B, the gene sets from each biological contrast of interest were used and each partition was summarized by the principal direction of variation foe each gene set. For the overall variability axis, the principal direction of variation for the entire set of cell samples was generated.

v) Trans-Activation of Genes by Donor Astrocyte RNA.

To select for genes that have significantly low expression in both astrocytes and neurons, for each of the 3104 informative genes, Fisher's combined P-value was computed for their expression rank in the 8 (neurons)+8 (astrocyte)=16 single-cell transcriptomes. The resulting p-values were multiple-test corrected for 3104 genes using Bonferroni correction and cutoff at the 5% significance level, which left 171 significantly low expressed genes. To assess significant up-regulation of these genes in 1 wk (9 cells), 2 wks (7 cells), 4 wks (11 cells), and N-TIPeR-N control cells (5 cells), pair-wise Welch's t-tests was carried out for increased expression for each of these cell types against the combined group of 16 astrocyte plus neurons. This analysis resulted in 49, 17, 24, and 0 significantly up-regulated genes at p<0.05 level for 1 week, 2 weeks, and 4 weeks TIPeRs, respectively, compared to the astrocytes and neurons. There were no (zero) significantly up-regulated genes at p<0.05 level for N-TIPeR-N controls, compared to the astrocytes and neurons.

The experimental results are now presented.

Experimental Example 1: Modeling of the Phototransfection of Complex RNA Populations To evaluate whether the astrocyte transcriptome can directly convert host neurons into astrocytes, the cell cultures were characterized to ensure the purity of the neurons that were to be transfected. A mixed culture (DIV 9) and a typical neuronal culture (DIV 2) were double-labeled using an antibody to microtubule-associated protein 2 (MAP2), which is a neuronal marker, and to glial fibrillary acidic protein (GFAP), which is an astrocyte marker. The data revealed that mixed cultures were immunoreactive for both MAP2 and GFAP. Notably, the young neuronal cultures were immunoreactive only for MAP2; these cultures were used in the subsequent TIPeR experiments below.

A TIPeR protocol was established which involved multiple RNA phototransfections over a 10-day period of time (FIG. 1A). Phototransfection was selected as the means to transfect the astrocyte transcriptome into neurons as it can transfect RNA into neurons with high efficiency (Barrett L E, et al. (2006) Region-directed phototransfection reveals the functional significance of a dendritically synthesized transcription factor. *Nat Methods* 3(6):455-460). To optimize for the amount of RNA that can be introduced into the host cells, the phototransfection of RNA transcripts that diffuse into the photoinduced pores in the cell membranes was modeled (FIGS. 2A and 2B). The process was modeled with an average transcript size of 1.5 kb+/−0.2 kb with the effective radius of the transcript determined by the Flory approximation ($R_{transcript} \sim 5.5 N^{1/3}$, where N is the size of the transcript in bases). Pore sizes were systematically varied to test the relative flux of transcriptome in a typical phototransfection experiment.

Simulations with the approximated transcriptome cargo revealed that a single sequence of sixteen pulses across the cell membrane would be sufficient to deliver a large number of transcripts while retaining their relative abundances (FIGS. 1B and 1C). There is a slight reduction in delivery efficiency of the largest transcripts expected, as their sizes are on the order of the assumed size of the phototransfection pore. For a transcriptome that contains a large range of transcript sizes, simulations indicated that the relative composition of the delivered cargo to the cytosol would remain largely remain intact. Based upon this simulation and empirical tests, 200 nanogram per microliter (ng/μl) concentration of poly-A+-selected RNA was used in these experiments. This is estimated to result in ~160,000 transcript molecules being delivered into the TIPeR cells in each phototransfection session; this number of transcripts is in excess of the normal contingent of mRNA transcripts of a hippocampal neuron (~100,000 molecules).

Experimental Example 2: Astrocyte mRNA TIPeRed Neurons Stably Express Donor Specific Astrocytic Markers Neuron cells transfected with astrocyte RNA are designated herein N-TIPeR-AS. The expression of the astrocytic marker GFAP and the neuronal marker MAP2 was assessed in the neurons TIPeRed with the astrocyte transcriptome. The individual N-TIPeR-AS cells were harvested at three time points (1, 2 and 4 weeks) following the third phototransfection (FIG. 1A). Nested single cell RT-PCR and sequence verification was then performed to assay GFAP and MAP2 mRNAs. Data in FIG. 3 show that 10 out of 26 N-TIPeR-AS cells across 4 weeks post-last phototransfection displayed GFAP gene expression. A subset of the GFAP expressing N-TIPeR-AS cells (8 cells) also expressed the neuronal MAP2 mRNA, suggesting that these cells were intermediate between neuronal and astrocytic phenotypes. Finally, two cells showed no detectable MAP2 gene expression in the RT-PCR assay, showing that MAP2 gene expression had been turned off in these two cells.

Figure 3B:
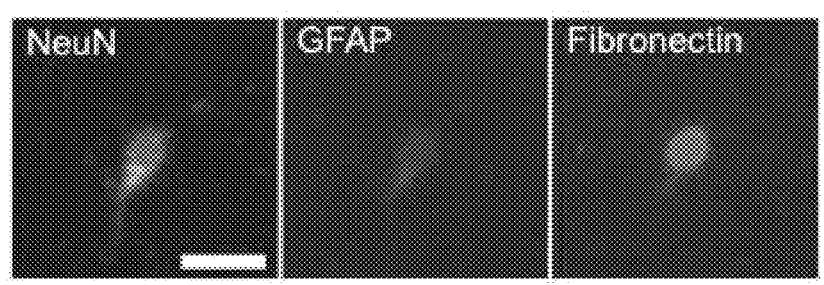
Figure 3C:
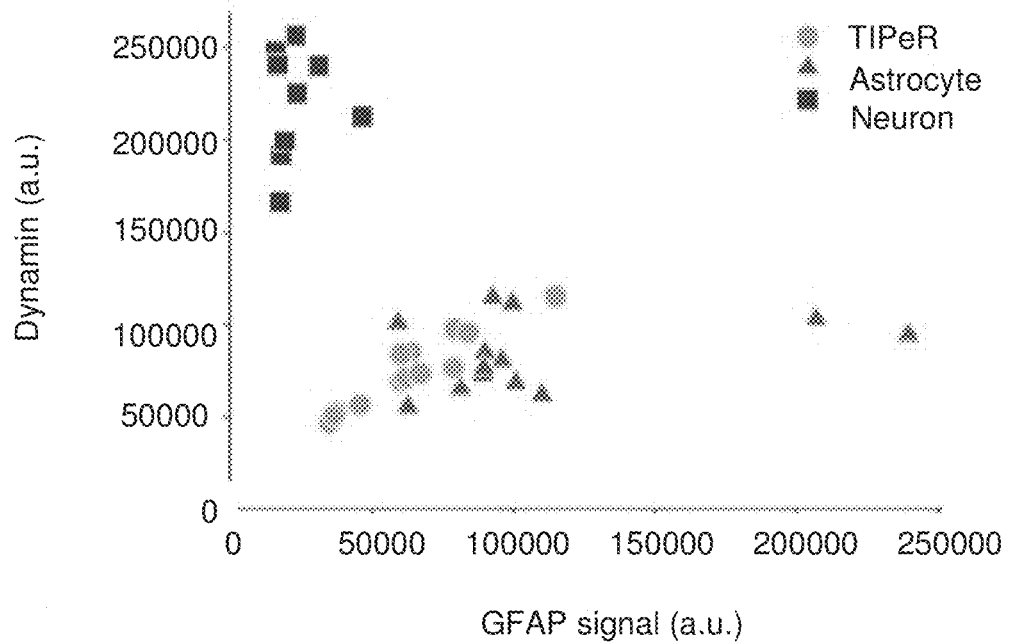

The N-TIPeR-AS cells were also assessed for expression of astrocytic protein markers. Triple-labeled immunocytochemistry was performed on the N-TIPeR-AS cells, using antibodies against the neuronal marker NeuN and the astrocytic marker GFAP. Also used was an antibody against the higher abundance astrocytic marker fibronectin, which is the seventh most abundant mRNA relative to GFAP, which is the $191^{st}$ most abundant mRNA, as observed in single astrocyte microarray analysis. No fibronectin mRNA or protein was detected in neurons. Immunocytochemical analysis of NeuN, GFAP and fibronectin in N-TIPeR-AS cells two weeks after the last phototransfection showed that astrocytic markers GFAP and fibronectin co-expressed with the neuronal marker NeuN (FIG. 3B). GFAP protein expression was low, while fibronectin was more abundant in these cells. Similar to the RT-PCR results, the N-TIPeR-AS cells co-expression of all three antigens suggests that the 2-week N-TIPeR-AS cells were at an intermediate phenotypic state between neurons and astrocytes. A distinct set of immunocytochemistry studies was also performed with the neuronal specific anti-Dynamin 1 antibody and anti-GFAP. To assess the expression levels, the integrated fluorescence signal strength of targeted cell area was analyzed (FIG. 3C). The results showed that the expression patterns of Dynamin 1 and GFAP of TIPeR cells were similar to that of astrocytes, while neurons had a distinctive pattern.

Experimental Example 3: N-TIPeR-AS Cells Display Global Alteration in Overall Gene Expression Profile Single-cell transcriptomes of neurons, astrocytes, control cells (neurons TIPeRed with neuron transcriptome; designated as N-TIPeR-N), and N-TIPeR-AS cells were assayed for gene expression. RNA from 48 individual cells was individually isolated, amplified, and assayed with Affymetrix Rat Genome 230 2.0 GeneChips.

FIG. 4A shows a cluster diagram of the single-cell transcriptomes for a set of 3104 informative genes and the bootstrap support of the clusters. Out of 27 N-TIPeR-AS cells, 12 (44%) cells consistently clustered with the astrocytes 91% of the time, indicating expression profiles similar to the normal variation in astrocytes. These 12 TIPeR cells are designated herein as astro-TIPeRs, while the other 15 N-TIPeR-AS cells that do not cluster with the astrocytes are designated herein as neuro-TIPeRs. Control cells (N-TIPeR-N) were distinct from astrocytes with only 3% of the bootstrap samples clustering control cells with astrocytes.

FIG. 4B shows a 3-dimensional projection of the 3104-gene transcriptome along three biologically meaningful directions: (1) genes differentiating astrocytes and neurons; (2) genes showing large N-TIPeR-AS variation; and (3) genes that are most variable in all cells. This 3-dimensional plot shows how the transcriptome of individual cells delimit variable but a distinct region of identity for each cell types (lightly shaded cloud around the composite cells). Any cell within this region of identity is classified phenotypically as the same cell type. The N-TIPeR-AS cell transcriptomes were measured at 1 week, 2 weeks, and 4 weeks after the third photo-transfection. Interestingly, 3/9 of the 1-week cells, 4/7 of the 2-week cells, and 5/11 of the 4-week cells fell into the astro-TIPeR category, thus exhibiting an increasing astrocytic conversion (30% to 50%) between 1 and 2 weeks post-transfection age (FIG. 4A).

Experimental Example 4: De Novo, Up- and Down-Regulation of Genes are Seen in TIPeR Cells To dissect the genes that differentiate successful TIPeR cells, paired comparisons were carried out between astro-TIPeR cells, neurons, and astrocytes. A total of 532 genes significantly distinguish neurons from astrocytes with at least 2-fold intensity difference. These 532 genes separated into four categories: (A) TIPeR expression=astrocytes≠neurons (201 probes), (B) TIPeR expression=neurons≠astrocytes (202 probes), (C) intermediate TIPeR expression (77 probes), and (D) TIPeR expression different from both neurons and astrocytes (32 probes). See FIG. 4C. A GO enrichment analysis was carried out to assess the functional significance of the four groups (FIG. 5).

The up-regulated genes in group (A) showed greatest enrichment in the transcriptional activity category (RNA Pol II activity, RNA metabolic process, nucleic acid binding, gene expression), while the down-regulated genes were most enriched in the cell division and cytokinesis categories, as well as transmembrane transporter activity. It should be noted that down-regulated cell division genes do not mean that cell division itself is inhibited in successful TIPeR cells (cf., p53's activity in cell proliferation). Group (B) genes represent genes that have failed to move towards astrocytes. These genes are enriched for glutamine metabolic process, spindle pole and chromosomes (up-regulated), as well as anti-oxidant pathways (down-regulated). Of the genes whose TIPeR expression is neither astrocyte-like nor neuron-like (group C), notable enrichment of intra-cellular membrane-bound organelle related processes were found.

Since the half-life of GFAP mRNA is 4 hours (Valles S, Pitrach J, Renau-Piqueras J, & Guerri C (1997) Ethanol exposure affects glial fibrillary acidic protein gene expression and transcription during rat brain development. *J. Neurochem* 69:2484-2493), the GFAP gene expression in N-TIPeR-AS cells at 4 weeks post-phototransfection (FIG. 3A) indicates that the GFAP gene was de novo trans-activated and that endogenous GFAP mRNA was made, as also seen by the changes in global gene expression (FIG. 4C). No de novo up-regulation is seen in control cells.

To further confirm trans-activation of genes by donor RNA, genes whose expression level was significantly low in both neurons and astrocytes were delineated. If any of these genes shows increased expression in N-TIPeR-AS cells distinct from control TIPeR cells, that result would indicate de novo up-regulation. Out of the 3104 informative genes, 171 genes were found that were quiescent in both neurons and astrocytes (p<0.05). For each of these genes, significant up-regulation (p<0.05) was tested in 1-week (n=9), 2-week (n=7), 4-week (n=11) N-TIPeR-AS cells, and in N-TIPeR-N control cells (n=5), respectively, against the astrocytes and neurons (n=16). Significant up-regulation was found for 49 (1wk), 17 (2 wk) and 24 (4 wk) genes in N-TIPeR-AS cells and none in N-TIPeR-N control cells (FIGS. 4D and 5). The 1 wk post-phototransfection N-TIPeR-AS cells showed the greatest number of significantly up-regulated genes. Since genes that are quiescent in the original astrocyte transcriptome were selected, the expression of these genes was expected to decrease in the N-TIPeR-AS cell with maturation of the re-programming process. This prediction was confirmed in 2 wk and 4 wk N-TIPeR-AS cells (FIG. 4D). Interestingly, GO ontology annotation suggests that the de novo up-regulated genes were enriched for chromosome and DNA metabolism related processes (FIGS. 6 and 7) indicating a chromosomal remodeling response to donor RNA. The set of 3104 informative genes already excluded genes involved in phototransfection-specific systemic effects, and no de novo upregulation in N-TIPeR-N controls was found. These results are consistent with transient up-regulation of a subset of genes soon after the introduction of new RNA, putatively induced by trans-factors translated from the donor RNA.

Experimental Example 5: Morphological Analysis of TIPeRed Cells

Figures 8A, 8B, 8C:
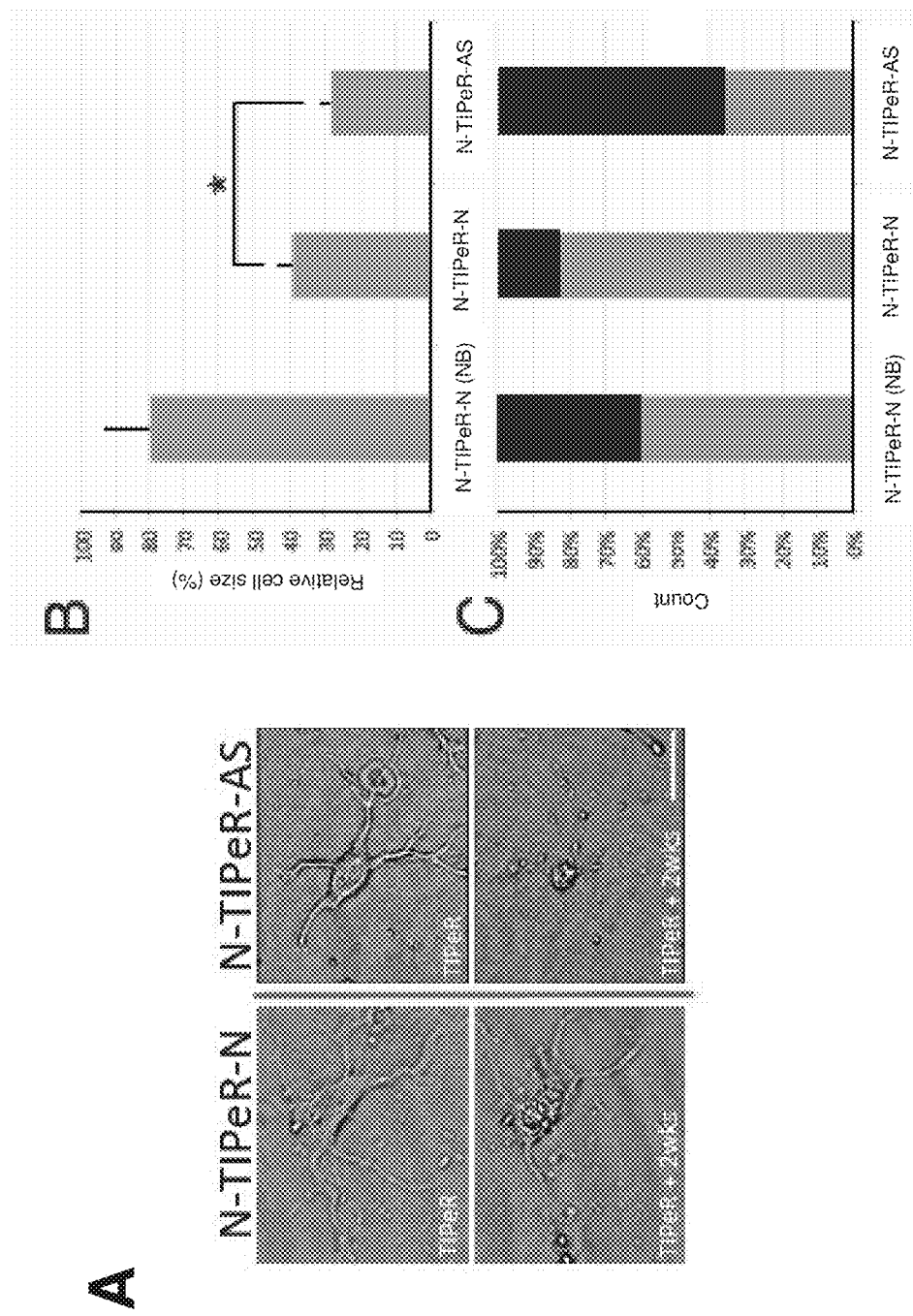
FIG. 8A-8C is a series of images and graphs depicting morphological analysis of TIPeR cells.

The morphology of the N-TIPeR-AS cells was assessed using MetaMorph software (Molecular Devices). The N-TIPeR-AS cells exhibited a substantial reduction in cellular size (72% reduction from initial cell size, n=27), including both soma and retained processes (FIG. 8B). Control N-TIPeR-N cells showed a smaller reduction in overall size when cultured in neuronal medium (21%, n=15) or when cultured in astrocyte medium (39%, n=29). In addition, there was a significant retraction of processes in the N-TIPeR-AS cells that was not observed in N-TIPeR-N neurons grown under either culture conditions. Data shown in FIG. 8C illustrates that over 60% of the N-TIPeR-AS cells retracted all processes, whereas only 12% and 37% of N-TIPeR-N control cells cultured in astrocyte medium and neuronal medium, respectively, show retracted processes morphologies. Thus, the astrocyte transcriptome appears to induce both a size reduction and a dramatic loss of the neuron-critical processes. The different morphological effects of the neuronal and astrocyte transcriptomes upon the same host cell type (hippocampal neuron) highlight the transcriptome specific effects. The N-TIPeR-AS cells showed a morphology that is smaller than that of a prototypical astrocyte. The culture conditions likely contribute to the observed morphology, as it is likely that re-plating after phototransfection would permit unconstrained membrane remodeling (Hanna J, et al. (2007) Treatment of sickle cell anemia mouse model with iPS cells generated from autologous skin. *Science* 318 (5858):1920-1923).

Experimental Example 6: N-TIPeR-AS Cells Display Astrocyte-Like Physiological Responses Cellular physiology results from the coordinate expression and function of multiple gene products. Given that the microarray data (FIG. 4) indicate the development of an astrocyte-like expression profile in the N-TIPeR-AS cells, it is useful to determine if this global change in gene expression results in an astrocyte-like physiology. Intracellular calcium plays an important role in physiological processes, and imaging of changes in intracellular calcium levels has been used to characterize unique neuronal and astrocytic physiologies (Rowe E W, Jeftinija D M, Jeftinija K, & Jeftinija S (2005) Development of functional neurons from postnatal stem cells in vitro. *Stem Cells* 23(8):1044-1049). Both neurons and astrocytes express glutamate receptors and show increased intracellular calcium when exposed to glutamate. Astrocytes, unlike neurons, do not show rapid calcium increases upon KCl application.

Figure 9:
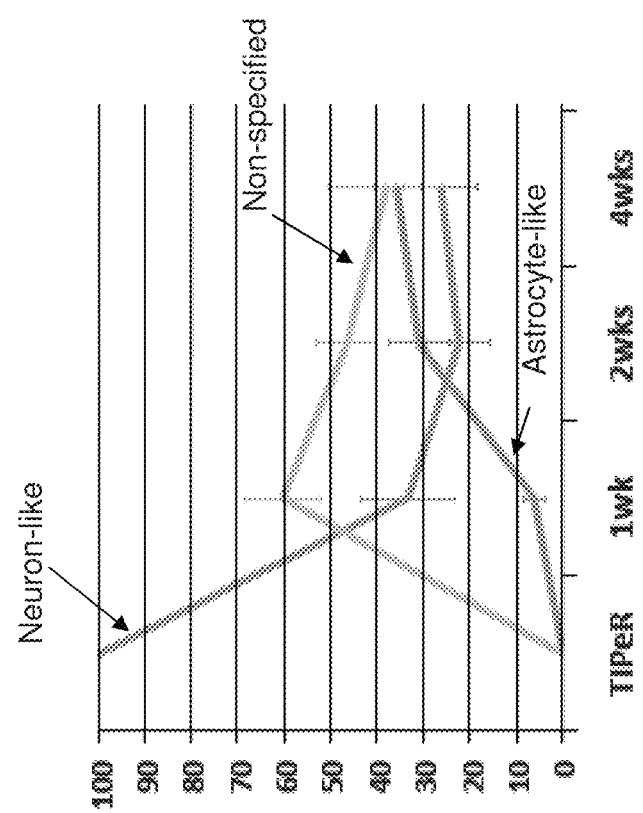
FIG. 9 is a graph of percentage of N-TIPeR-AS cells displaying various physiological calcium fluctuation patterns as a function of time post third phototransfection. "Astrocyte-like" refers to at least 5% increase in Fluo-4 intensity only upon glutamate (500 μM) but not KCl (50 mM) application in calcium fluctuation pattern. "Neuron-like" refers to at least at least 5% increase in Fluo-4AM intensity upon both glutamate and KCl application in calcium fluctuation patter. "Non-specified" N-TIPeR-AS cells are the cells that show no detectable change upon glutamate application. Error bars are the SEM.

As illustrated in FIG. 9, prior to TIPeR, 100% of the cells identified as neurons (25 out of 25 cells; designated pre-N-TIPeR-AS) displayed neuronal activity (calcium increases in response to both glutamate (500 µM) and KCl (50 mM) application). The percentage of cells with neuronal responses decreased to 33% (16 out of 48 cells) at 1 week, 22% (13 out of 58) at 2 weeks and 26% (11 out of 42) at 4 weeks after TIPeR. Cells displaying astrocyte-like activities (calcium increases only upon glutamate, but not KCl application) grew from 0% (0 out of 25 cells) before TIPeR to 6% (3 out of 48 cells) after 1 week, 31% (18 out of 58 cells) after 2 weeks and 36% (15 out of 42 cells) after 4 weeks. At the initiation of the TIPeR process, all the cells expressed host neuron-like physiological responses; with the passage of time, the number of N-TIPeR-AS cells showing neuron-like physiology decreased. As this decrease occurred, a population of cells that was physiologically undefinable as neurons or astrocytes became prominent at one week and then receded, as the number of physiologically astrocyte-like cells increased. This indeterminate physiology may represent the initial response of the neuronal hosts to TIPeR, which is also seen as Neuro-TIPeR cells in the microarray data (FIGS. 4A and 4C). These data suggest that the astrocyte-like physiology of the N-TIPeR-AS cells increases as a function of time post-phototransfection, in accord with the progression seen in the single cell RT-PCR and single cell expression profiling data.

Experimental Example 7: Preparation of Cardiomyocyte-Like Cells from Embryonic Fibroblasts Cardiomyocyte-like cells ("tCardiomyocytes") were created from mouse primary embryonic fibroblasts using the following materials and methods.

Cells:

Mouse Primary Embryonic Fibroblast (PMEF) was purchased from Millipore Corporation (Catalog number PMEF-NL) and incubated in Dulbecco's Modified Eagle Medium (DMEM) (Invitrogen) supplemented with 10% of fetal bovine serum (FBS) in the incubator (5% $CO_2$, 37° C.).

Primary cardiomyocyte cells were prepared from heart ventricles of mouse and frozen at −80° C.

mRNA Isolation:

Total RNAs were isolated from frozen mouse cardiomyocytes using TRIzol® Reagent (Invitrogen) and chloroform following manufacturer's protocol. mRNAs were extracted from the total RNA using Micro-FastTrack™ 2.0 mRNA isolation Kit (Invitrogen). Isolated mRNA was quantified using a NanoDrop spectrophotometer (Thermo Scientific). RNA integrity was examined using a 2100 BioAnalyzer (Agilent).

Transfection:

Mouse cardiomyocyte mRNA was transfected into PMEF using TransMessenger Transfection Reagent (Qiagen, Valencia, Calif.). In brief, 2 µg of mRNA was mixed with 4 µL of Enhancer R and then 8 µL of TransMessenger reagent was added to the mRNA-Enhancer R mixture. TransMessenger-mRNA complex was incubated with PMEF for 1 to 4 hours and washed. For mock transfection, an equal amount of yeast transfer RNA was used instead of cardiomyocyte mRNA. After the initial transfection, cells were cultured for 2 days and retransfected in the same manner. Immunocytochemistry was performed on the cultures 1 week, 2 weeks and 3 weeks post-first transfection.

Cell Culture:

Transfected cell cultures were incubated in 10% FBS-DMEM with 50 µM of Paclitaxel (Sigma-Aldrich) in a $CO_2$ incubator.

Immunocytochemistry:

Cardiomyocyte marker antibodies were purchased from commercial vendors: anti-MyoD1 antibody (Abcam); anti-connexin43/GJA1 Ab (Abcam); anti-NRx2.5 Ab (Abcam); and anti-cardiac Troponin I (Abcam).

Cells grown on glass-coverslips were fixed in 4% paraformaldehyde and permeabilized using 0.1% Triton X-100 in phosphate buffer saline. The cardiomyocyte marker antibodies were used in accordance with manufacturer's recommendation and hybridized at 4° C. for overnight. Alexa Fluor secondary antibodies (Invitrogen) were used to detect primary antibodies.

Cells were DAPI stained in accordance with a conventional protocol.

Imaging:

Zeiss LSM 5 confocal microscope system was used to take fluorescence images. Images were processed using MetaMorph® software (Molecular Devices, Silicon Valley, Calif.).

The results of this example are now discussed.

Figure 10:
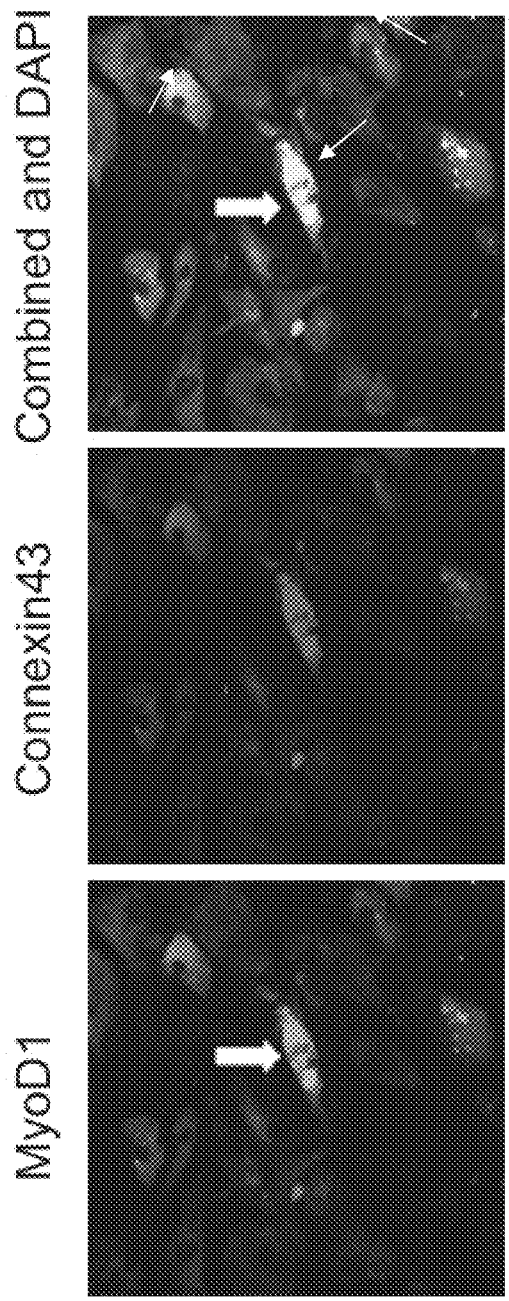
FIG. 10 is a series of three images of a representative TIPeRed cell that was immunostained for MyoD (left image) and Connexin43 (middle image). The right image combines the fluorescence for both the MyoD and Connexin43, with DAPI staining. The broad white arrows point to the nucleus of the cell. The narrow white arrows point to representative DAPI-stained DNA. The cell is a mouse embryonic fibroblast that was transfected twice with mouse cardiomyocyte mRNA, which was then immunostained two weeks after the first transfection.

The TIPeRed MEFs expressed muscle-specific antigens, including MyoD, Connexin43 and Troponin-1. See FIG. 10. The expression was localized in the appropriate cellular location. MyoD is a transcription factor that is expressed in cardiomyocytes which functions to direct the muscle cell development. Connexin 43 is a protein whose expression is enriched in native cardiomyocytes; it is involved in cardiac cell cytoarchitecture. Notably, tCardiomyocytes were observed to beat (e.g., rhythmically contract), as healthy, native cardiomyocytes do. In this experiment, approximately 5% of the cells were observed to convert to tCardiomyocytes.

Additional characterization of tCardiomyocytes will include one or both of the following: single cell microarray analysis on the TIPeRed cells, native cardiomyocytes and MEFs to ascertain the expression profile similarities and differences; and quantitative assessment of the ability of these cardiomyocyte-like cells to contract in response to stimulation, which is one of the physiological characteristics of cardiac muscle cells.

Experimental Example 8: Knock Out of CBP300 Using CRE Recombinase

An experiment was designed to assess whether individual genes could be knocked out in individual cells.

Mice engineered to have lox P sites flanking CBP300 were obtained from Ted Abel, University of Pennsylvania, Department of Biology. Cells were obtained from the mice by dissociation of the hippocampus as described in Buchhalter et al. (1991, *Brain Res Bull.* 26(3):333-338) and cultured. mRNA encoding CREe-recombinase was prepared by in vitro transcription from a Cre-recombinase cDNA-containing plasmid.

CRE-recombinase mRNA was introduced into individuals cells by lipid-mediated transfection, substantially as described in Experimental Example 7, with the exception that cells were transfect only once. In this experiment, two different concentrations of mRNA were used for transfection: 4.5 micrograms mRNA/250 microliter of TransMessenger Lipid and 45 micrograms RNA/250 ul of TransMessenger Lipid. CBP expression was evaluated in the nucleus of transfected cells by fluorescence microscopy at different times after transfection.

CBP expression was expected to completely disappear at some time after CRE recombinase mRNA translation. However, the rate and time of disappearance of CBP protein is expected to be affected by several factors, such as amount of intrinsic level and stability of CBP protein and mRNA. Furthermore, the amount of time needed for CRE recombinase to knockout the CBP gene is not known.

The results of this preliminary experiment suggest that this method was successful in excising a gene of interest from chromosomal material. Specifically, at 48 hours post-transfection, a distinct segregation of cells based on fluorescence intensity was not detected. However, at 7 days post-transfection, a difference between the transfected cells and non-transfected cells was observed. Images of representative cells are shown in FIG. 11. The extent of transfection was affected by the amount of mRNA used in the transfections. More transfected cells were observed for the higher quantity of RNA; these data are on the far left in FIG. 11. Lipid-mediated transfection is not an optimal transfection method because of limitations such as non-specific and uncontrollable transfection dosage. The knock out procedure described here is thus expected to benefit from the preferred method of transfection, phototransfection.

These data support that the method can be used successfully to prepare individual cells with a knock out, without requiring inducible promoters and their cognate inducers.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of transferring a phenotype of a first cell to a second cell, said method comprising
transfecting a second cell of a second cell type with an mRNA transcriptome of a first cell of a first cell type a first time, wherein the first cell type is different from the second cell type, wherein the mRNA transcriptome is locally administered to the second cell in vivo;
transfecting the second cell with an mRNA transcriptome of the first cell at least a second time wherein the mRNA transcriptome is locally administered to the second cell in vivo;
thereby initiating a change in physiology and morphology of the second cell, wherein the change in physiology and morphology yields a phenotype of the second cell that is indicative of the first cell,
wherein the first cell and second cell are selected from the group consisting of:
a) wherein the second cell is a fibroblast, and wherein the first cell is selected from the group consisting of an astrocyte, a cardiomyocyte, and a stem cell;
b) wherein the second cell is a neuron, and wherein the first cell is selected from the group consisting of an astrocyte and a cardiomyocyte; and
c) wherein the second cell is an astrocyte and wherein the first cell is a cardiomyocyte.

2. The method of claim 1, wherein said first cell type differs from said second cell type by one or more of: tissue type, differentiation degree, disease state, response to exposure to a toxin, response to exposure to a pathogen, and response to exposure to a candidate therapeutic.

3. The method of claim 1, wherein said mRNA transcriptome comprises mRNA transcripts having an average size between about 1 kb to about 5 kb.

4. The method of claim 1, wherein said transfecting step comprises irradiating said second cell with a laser, wherein said second cell is bathed in a fluid comprising said first cell mRNA transcriptome.

5. The method of claim 4, wherein said irradiating step comprises 2 to 25 laser excitation pulses, wherein said laser is directed to different sites on said second cell for each laser excitation pulse.

6. The method of claim 1, wherein said second cell is contacted with an exogenous transcription inhibition agent prior to said transfecting step.

7. The method of claim 1, wherein said second cell is not substantially contacted with an exogenous transcription inhibition agent before, during or after said transfecting step.

8. The method of claim 1, wherein said first cell and said second cell are each non-mammalian cells.

9. The method of claim 1, wherein said first cell and said second cell are each mammalian cells.

10. The method of claim 9, wherein the mammalian cell is a human cell.

11. The method of claim 1, wherein the method further comprises transfecting the second cell with one or more RNAs of the first cell, wherein the one or more RNAs comprise one or more exogenous nucleic acids selected from the group consisting of, siRNA, miRNA, hnRNA, tRNA, non-coding RNA and combinations thereof.

12. The method of claim 1, wherein the method causes the second cell to exhibit a change in one or more of gene expression, protein expression, immunological markers, synthesis of bioproducts, and membrane lipid composition.

13. The method of claim 12, wherein the method causes the second cell to exhibit a change in expression of at least 100 genes.

14. The method of claim 12, wherein the method causes the second cell to exhibit up-regulation of genes associated with chromosomal remodeling.

15. The method of claim 12, wherein at least about 5% of differentially expressed genes in said second cell change expression to a level observed for said first cell.

16. The method of claim 1, wherein the change in physiology and morphology of the second cell persists for at least 2 weeks.

17. The method of claim 16, wherein the change in physiology and morphology of the second cell persists for the lifetime of the cell.

18. The method of claim 1, wherein the second cell is a hair cell that responds to a first range of sound frequencies.

\* \* \* \* \*